(12) United States Patent
Pilato et al.

(10) Patent No.: US 6,610,848 B1
(45) Date of Patent: Aug. 26, 2003

(54) PLATINUM COMPLEX DIOXYGEN SENSORS

(75) Inventors: Robert S. Pilato, Silver Spring, MD (US); Neil V. Bough, Greenbelt, MD (US); Kelly Van Houten, Columbia, MD (US); Danica C. Heath, Greenbelt, MD (US)

(73) Assignee: Lumet LLC, Bethesda, MD (US)

( * ) Notice: Subject to any disclaimer, the term of this patent is extended or adjusted under 35 U.S.C. 154(b) by 0 days.

(21) Appl. No.: 09/361,173

(22) Filed: Jul. 27, 1999

Related U.S. Application Data

(60) Provisional application No. 60/094,270, filed on Jul. 27, 1998.

(51) Int. Cl.$^7$ ...................... C07D 213/04; C07D 213/32
(52) U.S. Cl. .................................. 546/2; 546/6; 546/22; 546/280.7; 546/339
(58) Field of Search .......................... 546/2, 22, 280.7, 546/6, 339; 544/225, 337, 353

(56) References Cited

U.S. PATENT DOCUMENTS

| | | |
|---|---|---|
| 3,509,026 A | 4/1970 | Sanders et al. |
| 3,612,866 A | 10/1971 | Stevens |
| 4,752,115 A | 6/1988 | Murray, Jr. et al. |
| 4,861,727 A | 8/1989 | Hauenstein et al. |
| 5,030,420 A | 7/1991 | Bacon et al. |
| 5,462,880 A | 10/1995 | Kane et al. |
| 5,567,598 A | 10/1996 | Stitt et al. |
| 5,718,842 A | 2/1998 | Papkovsky et al. |
| 5,728,422 A | 3/1998 | Kane et al. |
| 5,863,460 A | 1/1999 | Slovacek et al. |

OTHER PUBLICATIONS

Kelly A. Van Houten et al., "Synthesis and Characterization of α–Phosphorylated Ketones: Models for the Molybdopterin Precursor", Tetrahedron, 54, pp. 10973–10986 (1998).
Xiang–Ming Li et al., "Optical Characteristics of a Ruthenium(II) Complex Immobilized in a Silicone Rubber Film for Oxygen Measurement", Analyst, vol. 118, pp. 289–292 (1993).
Paul Hartmann et al., "Luminescence Quenching Behavior of an Oxygen Sensor Based on a Ru(II) Complex Dissolved in Polystyrene", Anal. Chem., vol. 67, pp. 88–93 (1995).
Dmitri B. Papkovsky et al., "Phosphorescent Complexes of Porphyrin Ketones: Optical Properties and Application to Oxygen Sensing", Anal. Chem., vol. 67, pp. 4112–4117 (1995).
Paul Hartmann et al., "Effects of Polymer Matrices on Calibration Functions of Luminescent Oxygen Sensors Based on Porphyrin Ketone Complexes", Anal. Chem., vol. 58, pp. 2615–2620 (1996).
John I. Peterson et al., "Fiber–Optic Probe for in Vivo Measurement of Oxygen Partial Pressure", Anal. Chem., vol. 56, pp. 62–67 (1984).

J.R. Bacon et al., "Determination of Oxygen Concentrations by Luminescence Quenching of a Polymer–Immobilized Transition–Metal Complex", Anal. Chem., vol. 59, pp. 2780–2785 (1987).
Wenying Xu et al., "Oxygen Sensors Based on Luminescence Quenching: Interactions of Metal Complexes with the Polymer Supports", Anal. Chem., vol. 66, pp. 4133–4141, (1994).
J.N. Demas et al., "Modeling of Luminescence Quenching–Based Sensors: Comparison of Multisite and Nonlinear Gas Solubility Models", Anal. Chem., vol. 67, pp. 1377–1380 (1995).
E.R. Carraway et al., "Photophysics and Photochemistry of Oxygen Sensors Based on Luminescent Transition–Metal Complexes", Anal. Chem., vol. 63, pp. 337–342 (1991).
Andrew Mills, "Controlling the Sensitivity of Optical Oxygen Sensors", ScienceDirect–Sensors and Actuators B: Chemical, vol. 51, Issue 1–3, pp. 60–68 (1998).
Andrew Mills et al., "Effect of Plasticizer Viscosity on the Sensitivity of an [Ru(bpy)$3^{2+}$(Ph$_4$B-)$_2$]–Based Optical Oxygen Sensor", Analyst, vol. 123, pp. 1135–1140 (1998).
Andrew Mills et al., "Effect of Plasticizer–Polymer compatibility on the Response Characteristics of Optical Thin CO$_2$ and O$_2$ Sensing Films", Analytica Chimica Acta, vol. 362, pp. 193–202 (1998).
Andrew Mills et al., "Fluorescence–Based Thin Plastic Film Ion–Pair Sensors for Oxygen", Analyst, vol. 122, pp. 63–68 (1997).
Andrew Mills et al., "Controlling the Response Characteristics of Luminescent Porphyrin Plastic Film Sensors for Oxygen", Anal. Chem., vol. 69, pp. 4653–4659 (1997).
Andrew Mills et al., "Chemical Influences on the Luminescence of Ruthenium Diimine Complexes and its Reponse to Oxygen", Thin Solid Films, vol. 306, pp. 163–170 (1997).
Arthur E. Colvin, Jr. et al., "A Novel Solid–State Oxygen Sensor", Johns Hopkins APL Technical Digest, vol. 17, No. 4, pp. 377–385 (1996).
Eric D. Lee et al., "Luminscence Ratio Indicators for Oxygen", Anal. Chem., vol. 59, pp. 279–283 (1987).
Kelly A. Van Houten et al., "Functionalized 2–Pyridyl–Substituted Metallo–1,2–Enedithiolates . . . ", Inorg. Chem. vol. 37, pp. 4647–4653 (1998).

(List continued on next page.)

*Primary Examiner*—Charandit S. Aulakh
(74) *Attorney, Agent, or Firm*—Venable LLP

(57) ABSTRACT

The luminescent platinum 1,2-enedithiolates are dual emitters with a short-lived $^1$ILCT* singlet and long-lived oxygen-sensing $^3$ILCT* triplet (ILCT; intraligand charge transfer transition) emissive excited states. Since only the triplet is quenched by molecular oxygen, the singlet serves as an internal standard for dioxygen measurements. This allows the concentration of dioxygen to be determined from the ratio of the singlet/triplet emissions. The novel dual emitters are readily polymer encapsulated to allow measurement of dioxygen in a range of settings. These polymer encapsulated dual emitters will serve as a drop-in step-out replacement sensor for currently available dioxygen measuring devices.

5 Claims, 5 Drawing Sheets

OTHER PUBLICATIONS

Ashutosh Sharma et al., "Unusually Efficient Quenching of the Fluorescence of a Energy Transfer–Based Optical Sensor for Oxygen", Analytica Chimica Acta, vol. 212, pp. 261–265 (1988).

Ashutosh Sharma et al., "Fiberoptic Oxygen Sensor Based on Fluorescence Quenching and Energy Transfer", Applied Spectroscopy, vol. 42, No. 6, pp. 1009–1011 (1988).

Sharada P. Kaiwar et al.; "Synthesis and Properties of Heterocyclic Substituted 1,2–Enedithiolates of Nickel, Palladium, and Platinum", Inorg. Chem., vol. 36, pp. 4234–4240 (1997).

Sharada P. Kaiwar et al., "Protonation–State–Dependent Luminescence and Excited–State Electron–Transfer Reactions of 2–and 4–Pyridine (–ium)–Substituted Metallo–1, 2–enedithiolates", Journal of the American Chemical Society, vol. 119, No. 39, pp. 9211–9214 (1997).

Sharada P. Kaiwar et al., "Excited State Properties of Quinoxaline–Substituted Platinum 1,2–Enedithiolates", J. Am. Chem. Soc., vol. 119, pp. 3311–3316 (1997).

Maria C. Moreno–Bondi et al., "Oxygen Optrode for Use in a Fiber–Optic Glucose Biosensor", Anal. Chem., vol. 62, pp. 2377–2380 (1990).

Otto S. Wolfbeis, "Oxygen Sensors", Fiber Optical Chemical Sensors and Biosensors, Chapter 10, vol. II, pp. 19–53.

Otto S. Wolfbeis et al., "Fiber–Optic Fluoresensor for Oxygen and Carbon Dioxide", Anal. Chem., vol. 60, pp. 2028–2030 (1988).

Otto S. Wolfbeis, et al., "Set of Luminescence Decay Time Based Chemical Sensors for Clinical Applications", ScienceDirect–Sensors and Actuators B:Chemical, vol. 51, Issue 1–3 (1998).

Vladimir I. Ogurtsov et al., "Selection of Modulation Frequency of Excitation for Luminescence Lifetime–Based Oxygen Sensors", ScienceDirect–Sensors and Actuators B:Chemical, vol. 51, Issue 1–3 (1998).

Max Schmidt et al., "Ethylenebis(diphenylphosphine)dihydrogensulfidenickel(II)", Inorganica Chimica Acta, pp. L19–L20, 32 (1979).

Max Schmidt et al., "Synthesis and Properties of Di–hydrogensulfido, Di–hydrogenselenido and Di–sodiumsulfido Complexes of Palladium(II) and Platinum(II)", Z. Naturforsch, 33b, pp. 1334–1337 (1978).

Julian A. Davies et al., "Hard Ligands as Donors to Soft Metals. Part 1. Formation of Oxygen–bonded Dimethyl Sulphoxide Complexes of Palladium(II) and Platinum(II) promoted by Steric Crowd", J.C.S. Dalton, pp. 1705–1708 (1978).

Otto S. Wolfbeis et al., "Fiber–Optic Fluorosensor for Oxygen and Carbon Dioxide", Anal. Chem, pp. 2028–2030 (1988).

John I. Peterson et al., "Fiber–Optic Probe for in Vivo Measurement of Oxygen Partial Pressure", Anal. Chem., Pages pp. 62–67 (1984).

Kelly A. Van Houten et al., "Functionalized 2–Pyridyl–Substituted Metallo–1,2–enedithiolates. Synthesis, Characterization, and Photophysical Properties of (dppe)M{$S_2C_2$(2–pyridine(ium)$CH_2$ $CH_2OR$)} and (dppe)M{[$S_2C_2$($CH_2$ $CH_2$–N–2–pyridium}]+ (R=H, Acetyl, Lauroyl; M=Pd, Pt; dppe=1,2–Bis(disphenylphosphino(ethane)", Inorg. Chem., 37, pp. 4647–4653 (1998).

Sharada P Kaiwar et al., "Excited State Properties of Quinoxaline–Substituted Platinum 1,2–Enedithiolates", J. Am. Chem. Soc. 119, pp. 3311–3316 (1997).

Robert S. Pilato et al., The Photophysical and Photochemical Properties of Metall–1,2–enedithiolates, Molecular and Supramolecular Photochemistry, pp. 1–35 (1998).

PLATINUM COMPLEX DIOXYGEN SENSORS

This application claims benefit of U.S. Provisional Application No. 60/094,270, filed Jul. 27, 1998.

FIELD OF THE INVENTION

The present invention relates to novel dual-emitting lumiphores, use of same in sensors, and methods for detecting dioxygen using the sensors.

TECHNOLOGY REVIEW

Oxygen is a critical element to many chemical processes on earth, including life itself. The capability of measuring the presence and concentration of oxygen is important to many fields of human endeavor.

Oxygen is generally found in the form of dioxygen, and this is the form in which it is generally measured. Dioxygen is an important analyte in human physiology, a commodity in the field of medicine, a measure of the health of the environment, and a necessary reagent in many industries. For the last three decades, dioxygen has been monitored with electrochemical sensors. Electrochemical sensors allow continuous monitoring of dioxygen. However, for a growing number of applications, electrochemical sensors have proven to be an unsatisfactory method of dioxygen measurement. This is because electrochemical sensors are prone to chemical and electrical interference; they consume dioxygen; and their bulk precludes miniaturization.

Optical sensors for dioxygen have overcome many of these problems found with electrochemical sensors. Importantly, they are also inexpensive and disposable. This allows greater flexibility of usage. For example, it is possible to couple optical sensors to the distal end of an optical fiber. Such systems offer remote, non-perturbing, multi-analyte analysis that can be used in a small, confined space, such as a blood vessel. (Wolfbeis, O. S.; Weis, L. J.; Leiner, M. J. P.; Zielgler, W. E. *Anal. chem.* 1988, 60, 2028–30 *Fiber-Optic Fluorosensor for Oxygen and Carbon Dioxide.*; Peterson, J. I.; Fitzgerald, R. V.; Buckhold, D. K. *Anal. Chem.* 1984, 56, 62–7 *Fiber-Optic Probe for in Vivo Measurement of Oxygen Partial Pressure.*; Xu, W.; McDonough, R. C.; Langsdorf, B.; Demas, J. N.; DeGraff, B. A. *Anal. chem.* 1994, 66, 4133–41 *Oxygen Sensors based on luminescence Quenching: Interactions of Metal Complexes with the Polymer supports.*; Lakowicz, J. R. *Topics In Fluorescence Spectroscopy*; Plenum Press: New York, 1994; Vol. 4.)

Most dioxygen optical sensors, including the sensor of the present invention, are based on a change in luminescence intensity emanating from a probe whose luminescence is quenched by molecular oxygen. The luminescent-probe molecules are usually encapsulated into a gas-permeable, ion-impermeable material. (Demas, J. N.; DeGraff, B. A.; Xu, W. *Anal. Chem.* 1995, 67, 1377–80 *Modeling of Luminescence Quenching-Based Sensors: comparison of Multisite and Nonlinear Gas Solubility Models.*; Mills, A.; Thomas, M. *Analyst* 1997, 122, 63–8 *Fluoresecence-based Thin Plastic film Ion-pair Sensors for Oxygen.*; Mills, A.; Thomas, M. D. *Analyst* 1998, 123, 1135–40 *Effect of Plasticizer viscosity on the sensitivity of an [Ru(bpy)32+(ph4B−)2]-based optical oxygen sensor.*; Mills, A. *Biosensors and Bioelectronics* 1998, 51, 60–8 *Controlling the sensitivity of optical oxygen sensors.*; Papkovsky, D. B.; Ponomarev, G. V.; Trettnak, W.; O'Leary, P. *Anal. Chem.* 1995, 67, 4112–7 *Phosphorescent Complexes of Porphyrin Ketones: Optical Properties and Application to Oxygen Sensing.*)

Most luminescent dioxygen sensing materials (for instance polymer films) rely on quenching of the emission from a polymer immobilized ruthenium(II) diamine complex or group VIII metalloporphyrins. While these materials have demonstrated the convenience of using luminescence quenching to measure dioxygen, they have many shortcomings. For example, currently available sensor molecules have a single, long-lived emission that is quenched by molecular oxygen. When fluorescence or phosphorescence intensity is used to measure oxygen quenching, such events as photo-bleaching, changes in optical clarity, and variations in the positioning of the film relative to the source and detector may interfere with accurate measurement. These must be minimized for accurate measurement. In addition, current optical sensors are not self-correcting for variations in intensity and, therefore, the sensor must be continually restandardized. (Bacon, J. R.; Demas, J. N. *Anal. chem.* 1987, 59, 2780–5 *Determination of Oxygen Concentrations by Luminescence Quenching of a Polymer-Immobilized Transition-Metal Complex.*; Carraway, E. R.; Demas, J. N.; DeGraff, B. A.; Bacon, J. R. *Anal. Chem.* 1991, 63, 337–342 *Photophysics and Photochemistry of Oxygen Sensors Based on Luminescent Transition-Metal Complexes*)

There have been extensive efforts to improve the reliability of these systems and to limit the need for restandardization, which have led to the measurement of excited state lifetimes. These lifetimes are commonly measured using frequency-modulated excitation and a phase-sensitive lock-in amplifier. As with intensity, the excited state lifetime of the emitter decreases upon exposure to molecular oxygen. This method is amenable for use with many emission molecules, including those described by the present invention. While measuring the phase change represents an effective method for dioxygen measurement, it requires a substantial complexity in the measuring device. This increase in complexity results in increased cost and decreased reliability. (Lakowicz, J. R. *Topics In Fluorescence Spectroscopy*; Plenum Press: New York, 1994; Vol. 4.; Hartmann, P.; Leiner, M. P. J.; Kohlbacher, P. *Biosensors and Bioelectronics* 1998, 51, 196–202 *Photobleaching of a ruthenium complex in polymers used for oxygen optodes and its inhibition by singlet oxygen quenchers.*; Thompson, R. B.; Lakowicz, J. R. *Anal. Chem.* 1993, 65, 853–856 *Fiber OPtic sensor based on phase fluorescence lifetimes.*; Wolfbeis, O. S.; Klimant, I.; Werner, T.; Huber, C.; Kosch, U.; Krause, C.; Neurauter, G.; Durkop, A. *Biosensors and Bioelectronics* 1998, 51, 17–24 *Set of Luminescence decay time based chemical sensors for clinical applications.*; Ogurtsov, V. I.; Papkovsky, D. B. *Biosensors and Bioelectronics* 1998, 51, 377–81 *Selection of modulation frequency of excitation for luminescence lifetime-based oxygen; Multimetallic and Macromolecular Inorganic Photochemistry in the Series Molecular and Supramolecular Photochemistry; The Photophysics and Photochemistry of 1,2-enedithiolates* Pilato, R. S. (Schanze, K.; Ramamurthy, V. ed.) 1999 vol. 4, Chpt. 5. pages 185–214 Marcel Dekker Inc., New York)

SUMMARY OF THE INVENTION

The present invention describes new dioxygen sensors based upon dual-emitting luminescent platinum 1,2-enedithiolates. By the nature of the dual emission, these sensors are more accurate, more reliable, and more versatile than those sensors considered current art.

The discovery of the dual-emitting complexes described eliminates the need for continual restandardization of the sensor and the need to use frequency modulation to measure dioxygen. In addition, these dual-emitting sensors can be easily adapted for use as simple inserts in common fluorescence cuvetts, which further expands their application.

DETAILED DESCRIPTION OF THE INVENTION

Figure 1:
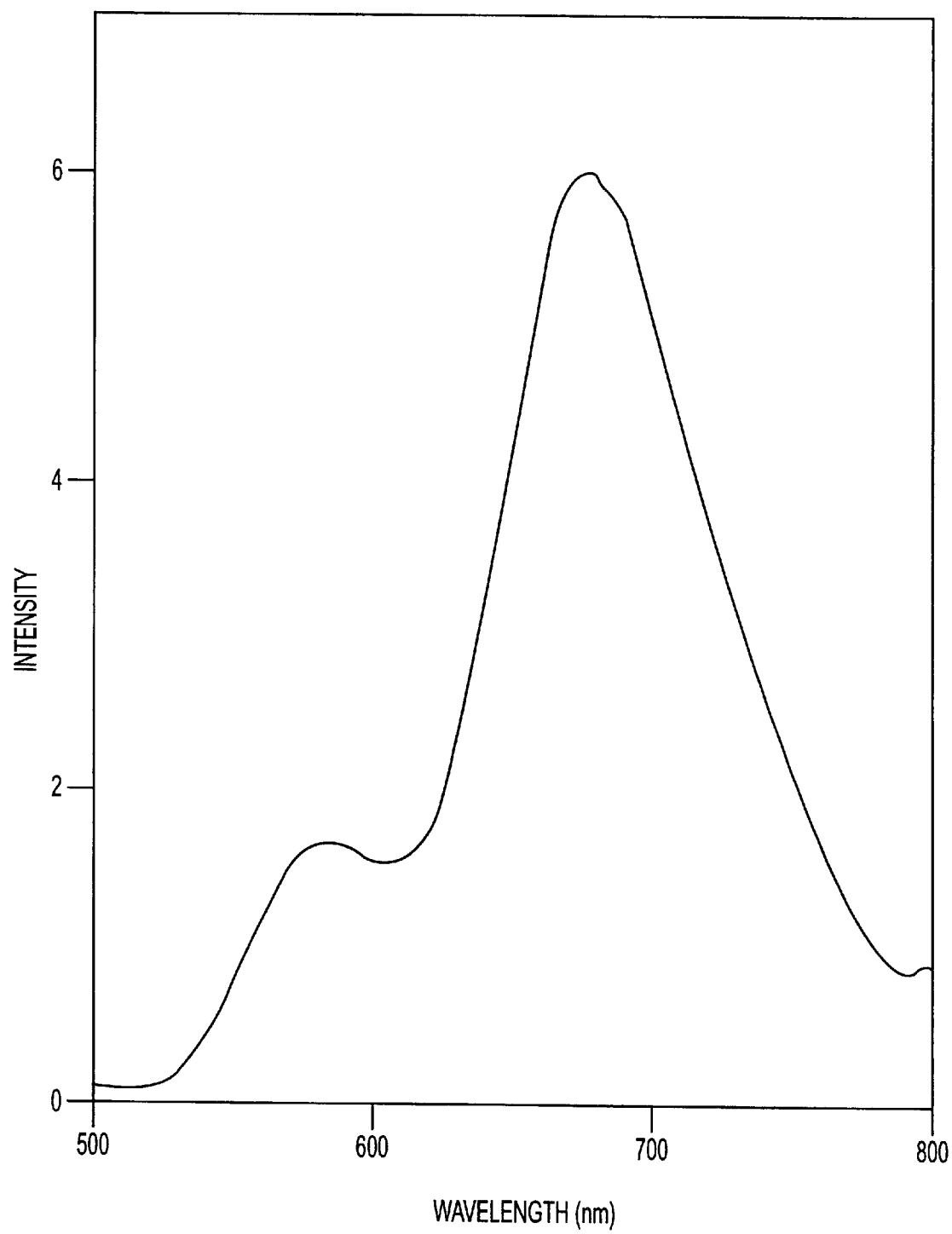
FIG. 1 is a typical emission spectra of Complex 1a in a GE RTV-118 Film (0.5 mm thick) at 0.1% loading. The film is mounted on a quartz slide, placed in a deoxygenated, water-filled cuvette, and held at approximately: 45° to the source and detector of a SLM-AB2 spectrofluorometer. The dual-emission maxima are found at 587 and 679 nm for the $^1$ILCT* and $^3$ILCT*, respectively.

The luminescent platinum 1,2-enedithiolates (complexes 1–4 below) of the invention are dual emitters. The emissions from these complexes arise from both an intraligand charge transfer (ILCT) transition singlet $^1$ILCT* and triplet $^3$ILCT*. Given the relative lifetimes of the singlet and triplet, only the emission from the $^3$ILCT* is quenched upon exposure to molecular oxygen at less than 10 M. As such, the $^3$ILCT* senses the quenching agent, $O_2$, while the $^1$ILCT* serves as an internal standard over a wide range of dioxygen concentrations. This allows the use of the $^1$ILCT*/$^3$ILCT* ratio (either intensity or area) for measuring dioxygen concentration. This is in contrast to measuring absolute emission intensity (or area) with a single emitter (the current art). Measuring the relative emission intensity or area of a dual emitter has many advantages over measuring absolute emission intensity or area. These advantages include: 1) allowing accurate measurements using standard fluorescence techniques; 2) increasing point-to-point accuracy; and 3) allowing degradation and photobleaching of the sensor to be monitored and accounted for without restandardization. While the advantages of a dual emitting dioxygen sensor are well known, few systems have been created. Such systems with a similar singlet/triplet intensity are rare and those systems studied (such as 4-bromo-1-naphthoyl derivatives) are not suitable for a broad spectrum of $O_2$ measurements including measurements of aqueous $O_2$. Coupling these sensors to the appropriate enzymes allows detection of $H_2O_2$, $O_2^-$ and a host of oxidase enzyme substrates and inhibitors (Kostov, Y; Van Houten, K. A., Harms, P.; Pilato, R. S.; Rao, G. "*Dioxygen Detection Utilizing A Dual Emitter and a Low-Cost Solid-State Ratiometric Fluorometer.*" Submission 1999, *Anal. Chem*: Van Houten, K. A.; Walters, K. A.; Schanze, K. S; Pilato, R. S. "*Transient Absorption Spectroscopic Studies of Platinum-1,2-enedithiolates.*" Submission 1999, *J. Fluorescence Spectroscopy*).

Molecules of the Current Invention

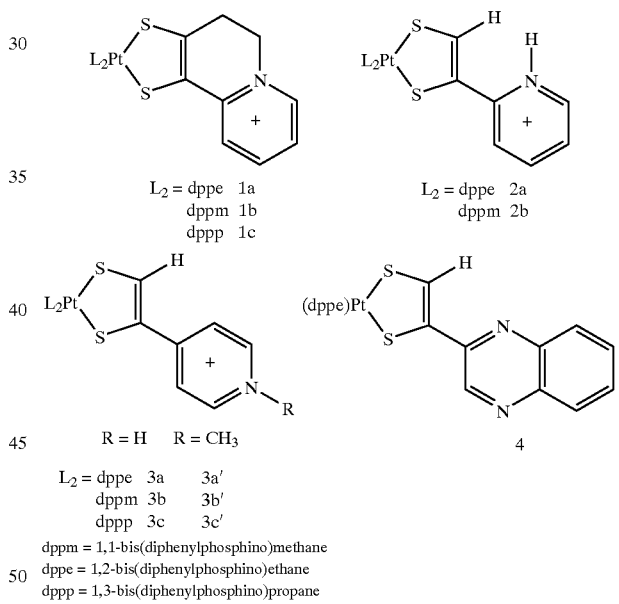

$L_2$ = dppe 1a
  dppm 1b
  dppp 1c $L_2$ = dppe 2a
  dppm 2b

R = H   R = CH$_3$ $L_2$ = dppe 3a   3a'
  dppm 3b   3b'
  dppp 3c   3c'

4 dppm = 1,1-bis(diphenylphosphino)methane
dppe = 1,2-bis(diphenylphosphino)ethane
dppp = 1,3-bis(diphenylphosphino)propane When immobilized in a host of polymer/plasticizer combinations, the sensing range of the platinum complexes of the invention can be varied, a finding with extensive literature precedent. Immobilization also limits access of other quenching agents to the $^3$ILCT*. This system is amenable to the accurate measurement of sub-micromolar $O_2$ changes which allows the measurement of biological dioxygen consumption and generation. The system is amenable for use with whole cells and proteins, including oxidases, peroxidases, dismutases, and catalases. Unlike all other known systems (ruthenium bipyridyl complexes and late transition metal porphryin complexes) and those used commercially, this system is not limited to use in fiber optic, diode, or phase-sensitive detectors, and can be used as a standard fluorescence cuvette insert. Unlike all "single"

emitting systems, the dual emitter is not sensitive to the angle of the source or detector allowing said use. (Van Houten, K. A.; Pilato, R. S. "Metallo-1,2-enedithiolates; Room Temperature Dual Emitters and Much More" Lumin. Forum 19995 #3; Kaiwar, S. P.; Hsu, J; Liable-Sands, L.; Rheingold, A. L.; Pilato, R. S. "The Synthesis and Characterization of Heterocyclic Substituted 1,2-Enedithiolates of Nickel, Palladium and Platinum" Inorg. Chem. 1997, 36, 4234)

The immobilized sensors can also be used as a fiber optic tip. The dual emitters allow the condition of the sensor to be monitored, and do not require recalibration of the sensor as the overall emission intensity drops due to optical changes and photobleaching. Since commercially available fiber optic dioxygen detectors use 470 nm excitation, which is within 20 nm of the excitation $\lambda_{max}$ of complexes 1–4, film containing these dual-emitting lumiphores can be used with commercially available detectors as a drop-in step-out technology.

This invention is not limited to the complexes shown, since both the 1,2-enedithiolate ligand and the phosphine ligand (dppe) are readily varied. As such, a host of phosphine-substituted platinum 1,2-enedithiolate of the type $L_2Pt\{S_2C_2(R)(R')\}$ having properties similar to complexes 1–4 are also contemplated. For instance, the ligand bis-1,2 (diphenyldiphos)phinoethane (dppe) can be replaced with bis-1,1 (diphenyldiphosphino)methane (dppm) or bis-1,3 (diphenyldiphosphino)propane (dppp). Alternatively, the ligands, $L_2$ may be phosphines, amines, or imines. The complexes shown and described are examples of readily prepared dppe substituted complexes, and this invention is not limited to these examples. (Sensor Technologies, "Dual-Emitter Molecules Monitor a Sensor's Condition", by Dexter Johnson, Wiley and Sons, NY. January, 1999)

In a preferred embodiment, the dioxygen sensor of the invention is composed of a dioxygen-quenchable platinum complex of the formula $L_2Pt\{S_2C_2(R)(R')\}$ that is immobilized in a polymer matrix. The polymer is transparent or substantially transparent to the excitation wavelength of the complex. The polymeric matrix is, of course, permeable to dioxygen so as to transfer dioxygen from the external environment to the sensor, i.e., platinum complex. Suitable polymers or polymer compositions include polymer cellulose acetates (CA), cellulose acetate, polysulfose butyrate (CAB), poly(styrene), poly(styrene)divinyl benzene, poly (methylmeth-acrylate), and silicone elastomers, such as GE RTV 118 which is used extensively in the art.

These polymers can be used in association with many plasticizers. Non-limiting examples of plasticizers are tributyl phosphate, or triethyl citrate. Such plasticizers can also be demonstrated to affect the sensitivity of the sensor.

The indicator polymer matrix can be affixed to an optical fiber. A popular configuration is to coat the end of an optical fiber with a film of polymer containing the complex (Peterson et. al. "Fiber-Optic Probe For in Vivo Measurement of Dioxygen Partial Pressure" Anal Chem. 1984 56, p 62–67). In a preferred embodiment, the devices can be manufactured into probes having 0.25 mm diameter plastic optical fibers (Crofon, DuPont). Smaller fibers can be used to make smaller probes, or a single fiber can be used with a suitable light-splitting system in an instrument to separate the excitation and emission light. A method of making bifurcated fibers has also been developed so that separate fibers leading to the light source and measurement system join and become a single fiber at the sensor end. (Application of Fluoresence Sensing to Bioreactor Rao, G.; BAmbot, S. B; Kwong, S. C. W.; Szmacinski, H.; Sipior, J.; Holavanahali, R.; Carter, G. In Topics in Fluorescence Spectroscopy, Vol.4 Probe Design and Chemical Sensing (Lakowicz, J. R., ed.) Plenum Publishing Co, New York, 1994, pp. 419–422)

These dual emitters can be used in systems that require a polymer-imbedded diode containing a sensing compound. The emission from the sensor is filtered and directed to a photomultiplier. Such devices can be miniaturized for use as sensing implants which have medical applications as disclosed by Colvin et al, "A Novel Solid State Dioxygen Sensor," John Hopkins APL Technical Digest, Vol 17, No. 4 (1996).

Synthesis of Complex Ia (dppe)$PtCl_2$ was first prepared according to the literature procedure (see Davies, J. A.; Hartley, F. R.; Murray, S. G. J.C.S. Dalton Trans. 1979, 1705–8). Platinum (II) chloride (1.5 g, 5.63 mmol) was dissolved in refluxing $CH_3CN$. To this solution was added diphenyldiphosphinoethane, dppe, (2.24 g 5.63 mmol, dppe was purchased from Acros) and the mixture was stirred at 25° C. for 1 hour. The volume of the solution was reduced and the mixture was filtered. The resulting solid was dried in vacuo to yield (dppe) $PtCl_2$ in 68% yield (2.58 g, 3.88 mmol). $^{31}$P NMR (DMSO-$d_6$): $\delta$43.3 (s with Pt satellites, $J_{Pt-P}$=2298 Hz). (dppm)$PtCl_2$ and (dppp)$PtCl_2$ are prepared in a manner similar to that described for (dppe)$PtCl_2$ by replacing dppe by bis (diphenyldiphoshino)methane (dppm) and 1,3-bis (diphenyldiphosphino)propane (dppp), respectively.

(dppe)Pt(SH)$_2$ was prepared by adapting the procedure for the analogous palladium compound (see Schmidt, M.; Hoffmann, G. G.; Holler, R. Inorg. Chim. Acta 1979, 32, L19–L20). A 0.20 M sodium hydrogensulfide solution was prepared by adding Na (0.07 g, 3.00 mmol) to 15 mL of absolute EtOH. Upon dissolution of the Na, the solution was exposed to $H_2S$ (1 Atm) for 1 hour. To this solution was added dppePtCl$_2$ to the above prepared (0.80 g, 1.21 mmol). The mixture was stirred under an $H_2S$ atmosphere for 24 hours, filtered, and washed with water (2×20 mL), ethanol (2×20 mL) and ether (2×20 mL). (dppe)Pt(SH)$_2$ was isolated in 50% yield (0.34 g, 0.61 mmol). $^{31}$P NMR (DMSO-$d_6$): $\delta$48.8 (s with Pt satellites, $J_{Pt-P}$=2882 Hz). (dppm)Pt(SH)$_2$ and (dppp)Pt(SH)$_2$ are prepared in a manner similar to (dppe)Pt(SH)$_2$ with the replacement of (dppe)$PtCl_2$ by (dppm)$PtCl_2$ and (dppp)$PtCl_2$, respectively.

(dppe)Pt(SH)$_2$ (250 mg, 0.379 mmol) and 1-(2-pyridyl)-2-bromo-4-acetoxy-butan-1-one (114 mg, 0.417 mmol) were stirred in DMF for 18 h. The DMF was removed in vacuo and the solid was chromatographed on a 1×20 cm alumina column where the product was eluted with $CH_2Cl_2$. The elutent was evaporated to dryness to give (dppe) Pt$\{S_2C_2$(2-pyridine) $(CH_2CH_2OAc)\}$ in 70% yield (266 mg, 0.265 mmol). A solution of 0.1 M $K_2CO_3$ in MeOH was used to dissolve (dppe)Pt$\{S_2C_2$(2-pyridine)$(CH_2CH_2OAc)\}$ (160 mg, 0.172 mmol). The solution was stirred at 25° C. for 1 hour, and the resulting mixture was concentrated in vacuo. The resulting solid was dissolved in $CH_2Cl_2$, washed with $H_2O$, and concentrated in vacuo to yield (dppe)Pt$\{S_2C_2$(2-pyridine)$(CH_2CH_2OH)\}$ in 91% yield (138 mg, 0.172 mmol). $^1$H NMR (CDCl$_3$): $\delta$8.34 (m, 1H, $C_5H_4N$), 7.82–7.75 (m, 8H, PC$_6H_5$ and 1H, $C_5H_4N$), 7.53–7.41 (m, 12H, PC$_6H_5$ and 1H, $C_5H_4N$), 7.02 (m, 1H, $C_5H_4N$), 3.94 (t, 2H, $CH_2O$, $J_{H-H}$=5 Hz), 2.90 (br t, 2H, $CH_2$, $J_{H-H}$=5 Hz), 2.68 (broad singlet, 1H, OH), 2.50 (m, 4H, PC$_2H_2$). $^{31}$P NMR (DMSO): $\delta$45.5 (d with Pt satellites, $J_{P-P}$=13 Hz; $J_{Pt-P}$=2722 Hz), 45.4 (d with Pt satellites, $J_{P-P}$=13 Hz; $J_{Pt-P}$=2722 Hz). IR (thin film, cm$^{-1}$): 3210 (w), 3053 (w), 2959 (w), 2851 (w), 1587 (s), 1542 (w), 1464 (w), 1435 (s), 1237 (m), 1104 (s). High resolution mass spectrum (FAB) calc. m/z=804.10498 for $C_{35}H_{32}ONP_2S_2{}^{196}Pt$; found 804.10785.

(dppe)Pt{$S_2C_2$(2-pyridine)($CH_2CH_2OH$)} was converted to the tetraphenyl borate salt [dppePt{$S_2C_2$($CH_2CH_2$-N-2-pyridinium)}][$BPh_4$], complex 1, as described below: (dppe)Pt{$S_2C_2$(2-pyridine)($CH_2CH_2OH$)} (0.200 g, 0.228 mmol) was dissolved in dry pyridine (10 mL) and cooled to −10° C. To this solution was added p-toluenesulfonylchloride (0.087 g, 0.456 mmol). The reaction mixture was allowed to warm to room temperature over 1 hour and the reaction was quenched by the addition of 1 mL of water. The pyridine solution was subsequently removed in vacuo. The resulting solid was dissolved in 5 mL of MeOH, to which 1 mL of a $NaBPh_4$ saturated MeOH solution was added. The tetraphenyl borate salt complex 1 was isolated in 56% yield (152 mg, 0.127 mmol) by filtration of the orange solid, which was washed with 3×5 mL of MeOH. $^1$H NMR ($CDCl_3$): δ8.49 (m, 1H, $C_5H_4N$), 7.62–7.58 (m, 8H, $PC_6H_5$, and 1H $C_5H_4N$), 7.45–7.37 (m, 12H, $PC_6H_5$ and 1H, $C_5H_4N$), 7.13–7.09 (m, 9H, $B(C_6H_5)_4$), 7.00 (m, 1H, $C_5H_4N$), 6.87–6.80 (m, 9H, $B(C_6H_5)_4$), 6.69–6.62 (m, 2H, $B(C_6H_5)_4$), 3.93 (t, 2H, $CH_2$, $J_{H-H}$=7 Hz), 2.60 (t, 2H, $CH_2$, $J_{H-H}$=7 Hz), 2.38 (m, 4H, $PC_2H_4$). $^{31}$P NMR (DMSO): δ47.3 (d with Pt satellites, $J_{P-P}$=13 Hz; $J_{Pt-P}$=2790 Hz), 47.2 (d with Pt satellites, $J_{P-P}$=13 Hz; $J_{Pt-P}$=2790 Hz). IR (thin film, cm$^{-1}$): 3054 (w), 2960 (w), 1620 (s), 1494 (s), 1435 (s), 1264 (m), 1104 (m). High-resolution mass spectrum (FAB) calc. m/z=787.11670 for $C_{35}H_{32}NP_2S_2{}^{195}Pt$; found 787.10992. It will be clear to one skilled in the art that a large number of emissive salts can be created by standard metathesis reactions (i.e., Replacements). The complexes [(dppm)Pt{$S_2C_2$($CH_2CH_2$-N-2-pyridinium)}][$BPh_4$], 1b, and 1c [(dppp)Pt{$S_2C_2$($CH_2CH_2$-N-2-pyridinium)}][$BPh_4$], 1c are prepared in a manner similar to 1a by replacing (dppe)Pt(SH)$_2$ with (dppm)Pt(SH)$_2$ and (dppp)Pt(SH)$_2$, respectively. (Van Houten, K. A.; Heath, D. C.; Barringer, C. A.; Rheingold, A. L; Pilato, R. S. "Functionalized 2-Pyridyl-Substituted Metallo-1,2-enedithiolates. Synthesis, Characterization, and Photophysical Properties of dppeM{S2C2(2-pyridine(ium)) (CH2CH2OR¢)} and dppeM{S2C2(CH2CH2-N-2-pyridinium)} where R¢=H, Acetyl, Lauroyl, M=Pd and Pt, and dppe=diphenyldiphosphinoethane." Inorg. Chem. 1998, 37, 4647.; Kaiwar, S. P.; Vodacek, A.; Blough, N.; Pilato, R. S. "Protonation State Dependent Emissions and Excited State State Electron Transfer Reactions of 2- and 4-Pyridine (ium) Substituted Metallo-1,2-Enedithiolates" J. Am. Chem. Soc. 1997, 119, 9211)

Synthesis of Complex 2

To a DMF (5 mL) solution of (dppe)Pt(SH)$_2$ (0.165 g, 0.25 mmol) was added 1-(pyridin-2-yl)-2-bromoethanone (0.062 g, 0.313 mmol). The solution became red over a period of 20 minutes. The DMF was removed from the resulting purple solution and the solid was washed with 3×20 mL of diethylether. The purple solid was dissolved in dichloromethane (5 mL) to which triethylamine was added dropwise until the solution was orange red. The solvent was removed and the solid was chromatographed on a 1×20 cm alumina column where the product eluted with 1:2 hexane:$CH_2Cl_2$. (dppe)Pt{$S_2C_2$(2-pyridine)(H)} was isolated as a yellow crystalline solid in 41% yield (78 mg, 0.10 mmol). Anal. calcd for $C_{33}H_{29}NP_2PtS_2$C, 52.04; H, 3.81; N, 1.84. Found: C, 51.88; H, 4.09; N, 1.57. $^1$H NMR ($CDCl_3$): δ8.38 (m, 1H, $C_5H_4N$), 7.96 (dd with $^{195}$Pt satellites, 1H, $S_2C_2H$, $J_{P-H}$=7 Hz; $J_{P-H}$=1 Hz; $J_{Pt-H}$=95 Hz), 7.88–7.79 (m, 8H, $PC_6H_5$), 7.69 (d, 1H, $C_5H_4N$, $J_{H-H}$=8 Hz), 7.57 (m, 1H, $C_5H_4N$), 7.52–7.46 (m, 12H, $PC_6H_5$), 6.94 (m, 1H, $C_5H_4N$), 2.55 (m, 2H, $PC_2H_2$), 2.51 (m, 2H, $PC_2H_2$). $^{31}$P NMR ($CDCl_3$): δ45.5 (d with Pt satellites, $J_{P-P}$=15 Hz; $J_{Pt-P}$=2770 Hz), 44.9 (d with Pt satellites, $J_{P-P}$=15 Hz; $J_{Pt-P}$=2730 Hz). Mass spectrum (FAB) m/z=761 (M$^+$), 593 (M$^+$ —$C_7H_5NS_2$). UV-Vis. [abs] $\lambda_{max}$ (ε) ($CH_2C_2$, nm): 358 (4300), 415 (sh, 380). IR (KBr, cm$^{-1}$): 3050 (w), 2963 (w), 2911 (w), 1578 (m), 1522 (m), 1508 (m), 1482 (m), 1459 (m), 1435 (vs), 1310 (w), 1284 (w), 1265 (w), 1207 (m), 1187 (m), 1104 (vs), 1050 (w), 1028 (w), 998 (m), 932 (w), 880 (m), 822 (m), 760 (w), 750 (m), 716 (s), 705(s), 690 (vs), 533 (vs), 486 (m).

(dppe)Pt{$S_2C_2$(2-pyridine)(H)} can be converted to corresponding pyridinium salt, Complex 2, by dissolving it in $EtO_2$ and exposing the solution to HCl. The red precipitate [(dppe)Pt{$S_2C_2$(2-pyridinium)(H)}][Cl] (complex 2) is collected by filtration and dried under a vacuum. [(dppe) Pt{$S_2C_2$(2-pyridinium)(H)}][Cl] can also be prepared by exposing film immobilized (dppe)Pt{$S_2C_2$(2-pyridine)(H)} to HCl gas. Complex 2b can be prepared in a manner similar to 2a by replacing (dppe)Pt(SH)$_2$ with (dppm)Pt(SH)$_2$.

Synthesis of Complex 3a

To a DMF (5 mL) solution of (dppe)Pt(SH)$_2$ (0.066 g, 0.1 mmol) was added 1-(pyridin-4-yl)-2-bromoethanone (0.025 g, 0.125 mmol). The solution became red over a period of 20 minutes. The DMF was removed from the resulting purple solution and the solid was washed with 3×20 mL of diethylether. The purple solid was dissolved in dichloromethane (5 mL) to which triethylamine was added dropwise until the solution was orange red. The solvent was removed in air, and the solid was chromatographed on a 1×20 cm alumina column where the product eluted with 1:2 hexane:$CH_2Cl_2$. (dppe)Pt{$S_2C_2$(4-pyridine)(H)} was isolated as a yellow solid in 38% yield (0.029 g, 0.038 mmol). Anal. calcd for $C_{33}H_{29}NP_2PtS_2$, C, 52.04; H, 3.81; N, 1.84. Found: C, 52.41; H, 3.87; N, 1.53. $^1$H NMR ($CDCl_3$): δ8.33 (d, 2H, $C_5H_4N$, $J_{H-H}$=6 Hz), 8.00 (d with $^{195}$Pt satellites, 1H, $S_2C_2H$, $J_{P-H}$=8 Hz; $J_{Pt-H}$=90 Hz,), 7.84–7.79 (m, 8H, $PC_6H_5$), 7.64 (d, 2H, $C_5H_4N$, $J_{H-H}$=6 Hz), 7.56–7.47 (m, 12H, $PC_6H_5$), 2.58 (m, 2H, $PC_2H_2$), 2.49 (m, 2H, $PC_2H_2$). $^{31}$P NMR ($CDCl_3$): δ45.4 (d with Pt satellites, $J_{P-P}$=14 Hz; $J_{Pt-P}$=2770 Hz), 44.9 (d with Pt satellites, $J_{P-P}$=14 Hz; $J_{Pt-P}$=2750 Hz). Mass spectrum (FAB) m/z=761 (M$^+$), 593 (M$^+$ —$C_7H_5NS_2$). UV-Vis. [abs] $\lambda_{max}$ (ε) ($CH_2Cl_2$, nm): 360 (3900), 410 (sh, 560). IR (KBr, cm$^{-1}$): 3047 (w), 2962 (w), 2919 (w), 1584 (s), 1541 (m), 1506 (s), 1484 (m), 1434 (vs), 1406 (m), 1308 (w), 1263 (w), 1206 (w), 1182(m), 1150 (w), 1099 (s), 1027 (m), 999 (m), 928 (m), 878 (m), 820 (m), 747 (s), 714 (s), 706 (s), 692 (vs), 528 (vs), 486 (m).

(dppe)Pt{$S_2C_2$(4-pyridine)(H)} can be converted to the corresponding pyridinium salt by dissolving it in $EtO_2$ and exposing the solution to HCl. The red precipitate [(dppe)Pt{$S_2C_2$(4-pyridinium)(H)}][Cl] can be collected by filtration and dried under a vacuum. [(dppe)Pt{$S_2C_2$(4-pyridinium)(H)}][Cl] can also be prepared by exposing film immobilized (dppe)Pt{$S_2C_2$(4-pyridine)(H), Complex 3, to HCl gas. [(dppm)Pt{$S_2C_2$(2-pyridinium)(H)}][$BPh_4$], 3b, and [(dppp)Pt{$S_2C_2$(2-pyridinium)(H)}][$BPh_4$], 3c, are prepared in a manner similar to 3a by replacing (dppe)Pt(SH)$_2$ with (dppm)Pt(SH)$_2$ and (dppp)Pt(SH)$_2$, respectively.

Synthesis of Complex 3a'

[(dppe)Pt{$S_2C_2$(4-pyridine)(H)}], (25 mg, 0.034 mmol) was dissolved in dry $CH_2Cl_2$ and methyl iodide (49 mg, 0.34 mmol) was added. The reaction mixture was stirred at 25° C. for 1 hour, and the reaction mixture was quenched by the addition of 1 mL of water. The $CH_2Cl_2$ solution was subsequently removed in vacuo. The resulting solid was dissolved in 5 mL of MeOH, to which 1 mL of a NaBPh$_4$ saturated MeOH solution was added. Complex 3a' was isolated as a red crystalline solid in 70% yield (25 mg, 0.023 mmol). $^1$H NMR (CDCl$_3$): δ8.34 (d with $^{195}$Pt satellites, 1H, J$_{P\text{-}H}$=6 Hz, S$_2$C$_2$H, J$_{Pt\text{-}H}$=96 Hz), 7.83–7.73 (m, 8H, PC$_6$H$_5$ and 2H C$_5$H$_4$N), 7.70–7.46 (m, 12H, PC$_6$H$_5$ and 2H C$_5$H$_4$N), 6.98–6.89 (m, 9H, B(C$_6$H$_5$)$_4$), 6.72–6.68 (m, 9H, B(C$_6$H$_5$)$_4$), 6.68–6.48 (m, 2H, B(C$_6$H$_5$)$_4$), 2.68 (s, 3H, CH$_3$), 2.44 (m, 4H, PC$_2$H$_4$). $^{31}$P NMR (CDCl$_3$): δ46.3 (q, second order spectrum with line spacings of 35 and 14 Hz and Pt satellites, J$_{Pt\text{-}P}$=2778 Hz). IR (thin film, cm$^{-1}$): 3055 (w), 2978 (w), 1630 (s), 1505 (s), 1486 (s), 1457 (s), 1433 (s), 1260 (m), 1193 (m), 1102 (s). High-resolution mass spectrum (FAB) calc. m/z=775.10992 for C$_{34}$H$_{32}$NP$_2$S$_2$$^{195}$Pt; found 775.10565.

[(dppm)Pt{S$_2$C$_2$(N-Me-4-pyridinium)(H)}][BPh$_4$], 3b' and [(dppp)Pt{S$_2$C$_2$(N-Me-4-pyridinium)(H)}][BPh$_4$], 3c' are prepared in a manner similar to 3a' by replacing (dppe)Pt(SH)$_2$ with (dppm)Pt(SH)$_2$ and (dppp)Pt(SH)$_2$, respectively.

Synthesis of Complex 4

To a DMF (5 mL) solution of (dppe)Pt(SH)$_2$ (132 mg, 0.20 mmol) was added 1-(quinoxylin-2-yl)-2-bromoethanone (53 mg, 0.21 mmol). The solution became purple over a period of 20 minutes. The DMF was removed from the resulting purple solution, and the solid was washed with 3×20 mL of diethylether. The purple solid was dissolved in dichloromethane (5 mL), to which triethylamine was added dropwise until the solution was orange red. The solvent was removed, and the solid was chromatographed on a 1×20 cm alumina column, where the product was eluted with 1:2 hexane:CH$_2$Cl$_2$. The eluent was evaporated to dryness to give complex 4, (dppe)Pt{S$_2$C$_2$(2-quinoxaline)(H)}·CH$_2$Cl$_2$ as an orange-red crystalline isolated in 40% yield (70 mg, 0.080 mmol) as the CH$_2$Cl$_2$ solvato aduct. Anal. calcd for C$_{37}$H$_{32}$Cl$_2$ N$_2$PtP$_2$S$_2$: C, 49.55; H, 3.57; N, 3.13. Found: C, 49.88; H, 3.31; N, 3.07. $^1$H NMR (CDCl$_3$): δ9.33 (s, 1H, C$_8$H$_5$N$_2$), 8.35 (d with Pt satellites, 1H, S$_2$C$_2$H, J$_{P\text{-}H}$=7 Hz; J$_{Pt\text{-}H}$=95 Hz), 7.97 (d, 1H, C$_8$H$_5$N$_2$, J$_{H\text{-}H}$=7 Hz), 7.89 (d, 1H, C$_8$H$_5$N$_2$, J$_{H\text{-}H}$=7 Hz), 7.83–7.77 (m, 8H, PC$_6$H$_5$), 7.58–7.51 (m, 2H, C$_8$H$_5$N$_2$), 7.50–7.44 (m, 12H, PC$_6$H$_5$), 2.51 (d, 4H, PC$_2$H$_2$, J$_{P\text{-}H}$=18 Hz; J$_{P\text{-}H}$=55 Hz). $^{31}$P NMR(CDCl$_3$): δ45.7 (d with Pt satellites, J$_{P\text{-}P}$=14 Hz; J$_{Pt\text{-}P}$=2780 Hz), 45.0 (d with Pt satellites, J$_{P\text{-}P}$=14 Hz; J$_{Pt\text{-}P}$=2728 Hz). Mass spectrum (FAB) m/z=812 (M$^+$), 594 (M$^+$ —C$_{10}$H$_6$N$_2$S$_2$). UV-Vis. abs. $\lambda_{max}$ (ε) (CH$_2$Cl$_2$, nm): 244 (29,900), 274 (26,800), 306 (8,400), 326 (9,400), 442 (6,000). IR (KBr, cm$^{-1}$): 3048 (w), 2947 (w), 2915 (w), 2849 (w), 1540 (m), 1506 (vs), 1483 (m), 1435 (vs), 1412 (w), 1330 (w), 1301 (w), 1280 (w), 1265 (m), 1207 (m), 1187 (w), 1131 (w), 1103 (s), 1027 (w), 999 (m), 920 (w), 879 (m) 855 (w), 820 (m), 799 (m), 750 (m), 748 (m), 714 (s), 690 (vs), 531 (vs), 484 (m).

Other Synthetic Methods (dppm)Pt(SH)$_2$

A 0.27 M sodium hydrogensulfide solution was prepared by adding Na (0.09 g, 3.85 mmol) to 15 mL of absolute EtOH. After the Na dissolved, the solution was exposed to H$_2$S (1 Atm) for 1 h. To this solution was added (dppm)PtCl$_2$ (1.00 g, 1.54 mmol). The mixture was stirred under an H$_2$S atmosphere for 24 h. The resulting solid was collected by filtration and washed with water (2×20 mL), ethanol (2×20 mL) and ether (2×20 mL). (dppm)Pt(SH)$_2$ was isolated in 70% yield (0.69 g, 1.08 mmol). $^1$H NMR (DMSO-d$_6$): δ7.84 (m, 8H, C$_6$H$_5$P), 7.51 (m, 12H, C$_6$H$_5$P), 4.90 (t, J$_{P\text{-}P}$=10 Hz, 2H, PCH$_2$P), −0.49 (d, second order spectrum with line spacing of 4 Hz and Pt satellites, J$_{Pt\text{-}H}$=28 Hz, 2H, SH). $^{31}$P NMR (DMSO-d$_6$): δ−50.9 (s with Pt satellites, J$_{Pt\text{-}P}$=2430 Hz). IR (thin film, cm$^{-1}$): 3849 (w), 3049 (w), 2966 (w), 1435 (s), 1261 (m), 1100 (s). High resolution mass spectrum (FAB) calc. m/z=645.04425 for C$_{25}$H$_{24}$P$_2$S$_2$$^{195}$Pt; found 645.04332.

(dppp)Pt(SH)$_2$

Prepared and isolated as described for (dppm)Pt(SH)$_2$ using Na (85 mg, 3.68 mmol) and (dppp)PtCl$_2$ (1.00 g, 1.46 mmol). (dppp)Pt(SH)$_2$ was isolated in 65% yield (0.59 g, 0.88 mmol). $^1$H NMR (DMSO-d$_6$): δ7.66 (m, 8H, C$_6$H$_5$P), 7.44 (m, 12H, C$_6$H$_5$P), 3.32 (m, 4H, C$_3$H$_6$P), 2.71 (m, 2H, C$_3$H$_6$P), −1.0 (d, second order spectrum with line spacing of 7 Hz and Pt satellites, J$_{Pt\text{-}H}$=26 Hz, 2H, SH). $^{31}$P NMR (DMSO-d$_6$): δ−0.97 (s with Pt satellites, J$_{Pt\text{-}P}$=2754 Hz). IR (thin film, cm$^{-1}$): 3849 (w), 3049 (w), 2917 (w), 1434 (s), 1262 (m), 1100 (s). High resolution mass spectrum (FAB) calc. m/z=673.07556 for C$_{27}$H$_{28}$P$_2$S$_2$$^{195}$Pt; found 673.07656.

(dppm)Pt{C$_2$S$_2$(2-pyridyl)(H)}, 5

To a DMF (5 mL) solution of (dppm)Pt(SH)$_2$ (250 mg, 0.156 mmol) was added 1-pyridin-2-yl-2-bromoethanone (46 mg, 0.233 mmol). The orange solution was stirred for 2 hours, becoming purple. The DMF was removed in vacuo and the solid was washed with 3×20 mL of diethyl ether. The purple solid was dissolved in dichloromethane (5 mL), and triethylamine was added dropwise to the solution until it was orange red. The solvent was removed, and the solid was chromatographed on a 1×20 cm alumina column, where the product eluted with CH$_2$Cl$_2$. The elutent was evaporated to dryness to give complex 5 as a yellow crystalline solid in 52% yield (60 mg, 0.080 mmol). $^1$H NMR (DMF-d$_7$): δ−8.53 (d, 1H, C$_5$H$_4$N, J$_{H\text{-}H}$=6 Hz), 8.21 (d with $^{195}$Pt satellites, 1H, J$_{P\text{-}H}$, 6 Hz, S$_2$C$_2$H), J$_{Pt\text{-}H}$=98 Hz), 7.91–7.81 (m, 8H, PC$_6$H$_5$ and 1H, C$_5$H$_4$N), 7.70 (m, 1H, C$_5$H$_4$N), 7.55 (d, 1H, C$_5$H$_4$N, J$_{H\text{-}H}$=6 Hz), 7.38–7.36 (m, 12H, PC$_6$H$_5$), 7.08 (m, 1H, C$_5$H$_4$N), 6.97 (d, 1H, C$_5$H$_4$N, J$_{H\text{-}H}$=6 Hz), 4.70 (t, 2H, PCH$_2$,PJ$_{P\text{-}H}$=11 Hz). $^{31}$P NMR (DMF-d$_7$): δ−45.7 (q, second order spectrum with line spacings of 74 and 67 Hz and Pt satellites, J$_{Pt\text{-}P}$=2314 Hz). IR (thin film, cm$^{-1}$): 3049 (w), 2959 (w), 1579 (m), 1461 (s), 1436 (s), 1276 (m), 1101 (s). High-resolution mass spectrum (FAB) calc. m/z= 746.07080 for C$_{32}$H$_{27}$NP$_2$S$_2$$^{195}$Pt; found 746.07334. UV-Vis ($\lambda$(nm), ε, CH$_2$Cl$_2$): 5, 355 (5000), 415 (900); 5H$^+$, 334 (6500), 449 (5100).

(dppp)Pt{C$_2$S$_2$(2-pyridyl)(H)}, 7

Prepared and isolated as described for complex 5 using (dppp)Pt(SH)$_2$ (100 mg, 0.149 mmol) and 1-pyridin-2-yl-2-bromoethanone (44 mg, 0.223 mmol). Complex 7 was isolated as a yellow crystalline solid in an 81% yield (93 mg, 0.12 mmol). $^1$H NMR (CDCl$_3$): δ8.34 (m, 1H, C$_5$H$_4$N), 8.17 (d with $^{195}$Pt satellites, S$_2$C$_2$H, J$_{P\text{-}H}$=5 Hz, J$_{Pt\text{-}H}$=88 Hz), 7.61–7.51 (m, 8H, PC$_6$H$_5$), 7.72 (m, 1H, C$_5$H$_4$N), 7.43–7.26 (m, 12H, PC$_6$H$_5$ and 1H, C$_5$H$_4$N), 6.84 (m, 1H, C$_5$H$_4$N), 2.69 (m, 4H, PC$_2$H$_2$), 2.57 (m, 2H, PC$_2$H$_2$). $^{31}$P NMR (DMF-d$_7$): δ−3.85 (q, second order spectrum with line spacings of 7 and 37 Hz and Pt satellites, J$_{Pt\text{-}P}$=2642 Hz). IR (thin film, cm$^{-1}$): 3049 (w), 2943 (m), 1644 (s), 1579 (m), 1520 (w), 1460 (w), 1435 (s), 1264 (m), 1102 (s). High resolution mass spectrum (FAB) calc. m/z=775.10992 for C$_{34}$H$_{32}$NP$_2$S$_2$$^{195}$Pt; found 775.10790. UV-Vis ($\lambda$(nm), ε, CH$_2$Cl$_2$): 7, 355 (6400), 410 (800); 7H$^+$, 334 (7000), 464 (5300).

(Ph$_3$P)$_2$Pt{C$_2$S$_2$(2-pyridyl)(H)}, 8

Prepared and isolated as described for complex 5 using (Ph$_3$P)$_2$Pt(SH)$_2$ (250 mg, 0.318 mmol) and 1-pyridin-2-yl-2-bromoethanone (95 mg, 0.478 mmol). Complex 8 was isolated as a yellow crystalline solid in 60% yield (169 mg, 0.19 mmol). $^1$H NMR (CDCl$_3$): δ8.34 (m, 1H, C$_5$H$_4$N), 7.65 (m, 1H, C$_5$H$_4$N), 7.53–7.42 (m, 15H, PC$_6$H$_5$ and 1H, C$_5$H$_4$N), 7.28–7.26 (m, 8H, PC$_6$H$_5$ and 1H, S$_2$C$_2$H), 7.17–7.12 (m, 15H, PC$_6$H$_5$ and 1H, C$_5$H$_4$N). $^{31}$P NMR (CDCl$_3$): δ20.2 (q, second order spectrum with line spacings of 27 and 65 Hz and Pt satellites, J$_{Pt-P}$=2868 Hz). IR (thin film, cm$^{-1}$): 3060 (w), 2955 (w), 1672 (m), 1578 (m), 1525 (m), 1455 (w), 1435 (s), 1261 (s), 1094 (s), 1020 (m). High-resolution mass spectrum (FAB) calc. m/z=887.14124 for C$_{43}$H$_{36}$NP$_2$S$_2$$^{195}$Pt; found 887.14452. UV-Vis (λ(nm), ε, CH$_2$Cl$_2$): 8, 359 (6100), 415 (1400); 8H$^+$, 335 (6800), 472 (5400).

(Pr$_3$P)$_2$Pt{C$_2$S$_2$(2-pyridyl)(H)}, 9

To a DMF (1 mL) solution of (Ph$_3$P)$_2$Pt{C$_2$S$_2$(2-pyridyl)(H), 8, (20 mg, 0.02 mmol) was added tri-n-propylphosphine (23 μL, 0.11 mmol). The solution was heated at 80° C. for 1 hour. The DMF was removed in vacuo, and the solid was chromatographed on a 1×5 cm alumina column, where the product eluted with CH$_2$Cl$_2$. The elutent was evaporated to dryness to give 9 as a crystalline solid in 52% yield (7 mg, 0.01 mmol). $^1$H NMR (CDCl$_3$): δ8.53 (m, 1H, C$_5$H$_4$N), 7.76–7.45 (m, 2H, C$_5$H$_4$N and S$_2$C$_2$H), 7.35 (m, 1H, C$_5$H$_4$N), 7.04 (m, 1H, C$_5$H$_4$N), 2.11–1.94 (m, 12H, CH$_2$P), 1.63–1.53 (12H, CH$_2$), 1.08–1.01 (m, 18H, CH$_3$). $^{31}$P NMR (CDCl$_3$): δ–2.85 (q, second order spectrum with line spacings of 33 and 27 Hz and Pt satellites, J$_{Pt-P}$=2714 Hz). IR (thin film, cm$^{-1}$): 2960 (w), 2929 (w), 2870 (w), 1698 (m), 1651 (m), 1575 (m), 1520 (m), 1455 (w), 1458 (s), 1076 (s). High resolution mass spectrum (FAB) calc. m/z=683.23511 for C$_{25}$H$_{48}$NP$_2$S$_2$$^{195}$Pt; found 683.23566. UV-Vis (λ(nm), ε, CH$_2$Cl$_2$): 9, 356 (4000), 412 (560); 9H$^+$, 339 (1200), 464 (4500).

(Ph$_2$MeP)$_2$Pt{C$_2$S$_2$(2-pyridyl)(H)}, 10

Prepared and isolated as described for complex 9 using (Ph$_3$P)$_2$Pt{C$_2$S$_2$(2-pyridyl)(H), 8, (20 mg, 0.02 mmol) and diphenylmethylphosphine (21 μL, 0.11 mmol). Complex 10 was isolated as a crystalline solid in 47% yield (7 mg, 0.009 mmol). $^1$H NMR (CDCl$_3$): δ8.61 (m, 1H, C$_5$H$_4$N), 7.96 (m, 1H, C$_5$H$_4$N), 7.76–7.60 (m, 8H, PC$_6$H$_5$ and 1H, S$_2$C$_2$H), 7.57–7.28 (m, 12H, PC$_6$H$_5$ and 1H, C$_5$H$_4$N), 7.09 (m, 1H, C$_5$H$_4$N), 1.85–1.69 (6H, CH$_3$P). $^{31}$P NMR (CDCl$_3$): δ–1.21 (q, second order spectrum with line spacings of 30 and 24 Hz and Pt satellites, J$_{Pt-P}$=2813 Hz). IR (thin film, cm$^{-1}$): 3051 (w), 2962 (w), 1596 (m), 1508 (m), 1437 (m), 1380 (m), 1262 (m), 1028 (m), 825 (m). 747 (m). High-resolution mass spectrum (FAB) calc. m/z=763.10992 for C$_{33}$H$_{32}$NP$_2$S$_2$$^{195}$Pt; found 763.10729. UV-Vis (λ(nm), ε, CH$_2$Cl$_2$): 10, 355 (4700), 415 (1100); 10H$^+$, 334 (4400), 462 (4000).

(Me$_2$PhP)$_2$Pt{C$_2$S$_2$(2-pyridyl)(H)}, 11

Prepared and isolated as described for complex 9 using (Ph$_3$P)$_2$Pt{C$_2$S$_2$(2-pyridyl)(H), 8, (20 mg, 0.02 mmol) and dimethylphenylphosphine (16 mg, 0.011 mmol). Complex 11 was isolated as a crystalline solid in 56% yield (8 mg, 0.01 mmol). $^1$H NMR (CDCl$_3$): δ8.61 (m, 1H, C$_5$H$_4$N), 8.05 (m, 1H, C$_5$H$_4$N), 7.76–7.28 (m, 10H, PC$_6$H$_5$, 1H, C$_5$H$_4$N, and 1H S$_2$C$_2$H), 7.07 (m, 1H, C$_5$H$_4$N), 1.90–1.61 (12H, CH$_3$P). $^{31}$P NMR (CDCl$_3$): δ–17.4 (q, second order spectrum with line spacings of 31 and 29 Hz and Pt satellites, J$_{Pt-P}$32 2762 Hz). IR (thin film, cm$^{-1}$): 3049 (w), 2966 (w), 1578 (m), 1522 (s), 1437 (s), 1381 (s), 1262 (m), 1105 (m), 1028 (m), 911 (m). 743 (m). High resolution mass spectrum (FAB) calc. m/z=639.07861 for C$_{23}$H$_{28}$NP$_2$S$_2$$^{195}$Pt; found 639.08279. UV-Vis (λ(nm), ε, CH$_2$Cl$_2$): 11, 351 (1700), 409 (506); 11H$^+$, 355 (1600), 457 (1600).

(dppm)Pt{S$_2$C$_2$(2-pyridyl)(CH$_2$CH$_2$OAc)}, 12

To a DMF (5 mL) solution of (dppm)Pt(SH)$_2$ (250 mg, 0.388 mmol) was added 1-(2-pyridyl)-2-bromo-4-acetoxybutan-1-one (333 mg, 1.16 mmol). The orange solution was stirred for 2 hours and became purple. The DMF was removed in vacuo and the solid was chromatographed on a 1×20 cm alumina column, where the product eluted with CH$_2$Cl$_2$. The elutent was evaporated to dryness to give 12 as a yellow crystalline solid in 65% yield (210 mg, 0.252 mmol). $^1$H NMR (CDCl$_3$): δ8.71 (m, 1H, C$_5$H$_4$N), 7.90–7.81 (m, 8H, PC$_6$H$_5$ and 1H, C$_5$H$_4$N), 7.64 (m, 1H, C$_5$H$_4$N), 7.53–7.33 (m, 12H, PC$_6$H$_5$), 7.10 (m, 1H, C$_5$H$_4$N), 4.56 (t, 2H, PCH$_2$, J$_{P-H}$=11 Hz), 4.49 (t, 2H, CH$_2$O, J$_{H-H}$=6 Hz), 3.14 (t, 2H, CH$_2$, J$_{H-H}$=6 Hz), 1.85 (s, 3H, CH$_3$). $^{31}$P NMR (CDCl$_3$): δ–46.2 (q, second order spectrum with line spacings of 48 and 13 Hz and Pt satellites, J$_{Pt-P}$=2364 Hz). IR (thin film cm$^{-1}$): 3054 (w), 2961 (w), 1738 (s), 1697 (s), 1582 (m), 1463 (w), 1436 (w), 1242 (s), 1139 (m). High-resolution mass spectrum (FAB) calc. m/z=833.11542 for C$_{36}$H$_{34}$O$_2$NP$_2$S$_2$$^{195}$Pt; found 833.11955. UV-vis (λ(nm), ε, CH$_2$Cl$_2$): 12, 345 (4500), 406 (480); 12H$^+$, 333 (9600), 453 (2100).

(dppp)Pt{S$_2$C$_2$(2-pyridyl)(CH$_2$CH$_2$OAc)}, 14

Prepared as described for complex 12 using complex 3 (250 mg, 0.371 mmol) and 1-(2-pyridyl)-2-bromo-4-acetoxybutan-1-one (211 mg, 0.723 mmol). Complex 14 was isolated in 71% yield (226 mg, 0.263 mmol). $^1$H NMR (CDCl$_3$): δ8.46 (m, 1H, C$_5$H$_4$N), 8.09 (m, 1H, C$_5$H$_4$N), 7.87–7.83 (m, 8H, PC$_6$H$_5$), 7.53 (m 1H, C$_5$H$_4$N), 7.51–7.31 (m, 12H, PC$_6$H$_5$), 6.96 (m, 1H, C$_5$H$_4$N), 4.10 (t, 2H, CH$_2$O, J$_{H-H}$=7 Hz), 2.96 (t, 2H, CH$_2$, J$_{H-H}$=76 Hz), 2.85 (m, 4H, PC$_3$H$_6$), 2.16 (m, 2H, PC$_3$H$_6$), 1.85 (s, 3H, CH$_3$). $^{31}$P NMR (CDCl$_3$): δ–4.75 (br s, with Pt satellites, J$_{Pt-P}$=2642 Hz); IR (thin film cm$^{-1}$): 3060 (w), 2955 (w), 1732 (s), 1694 (s), 1645 (m), 1539 (m), 1463 (w), 1436 (w), 1361 (w), 1245 (s), 1101 (m). High-resolution mass spectrum (FAB) calc. m/z=861.14673 for C$_{38}$H$_{38}$O$_2$NP$_2$S$_2$$^{195}$Pt; found 861.15245. UV-vis (λ(nm), ε, CH$_2$Cl$_2$): 14, 343 (4200), 405 (490); 14H$^+$, 330 (8500), 462 (1800).

(dppm)Pt{S$_2$C$_2$(2-pyridyl)(CH$_2$CH$_2$OH)}, 15

To a solution of 0.1 M K$_2$CO$_3$ in MeOH was added complex 12 (210 mg, 0.252 mmol). The solution was stirred at 25° C. for 1 hour and the resulting mixture was concentrated in vacuo. The resulting solid was dissolved in CH$_2$Cl$_2$, washed with H$_2$O, and concentrated in vacuo to yield complex 15 in 91% yield (191 mg, 0.251 mmol). $^1$H NMR (CDCl$_3$): δ8.29 (m, 1H, C$_5$H$_4$N), 7.84–7.71 (m, 8H, PC$_6$H$_5$ and 1H, C$_5$H$_4$N), 7.38–7.25 (m, 12H, PC$_6$H$_5$ and 1H, C$_5$H$_4$N), 6.98 (m, 1H, C$_5$H$_4$N), 4.62 (t, 2H, PCH$_2$, J$_{P-H}$=11 Hz), 3.97 (t, 2H, CH$_2$O, J$_{H-H}$=7 Hz), 2.99 (t, 2H, CH$_2$, J$_{H-H}$=7 Hz. $^{31}$P NMR (CDCl$_3$): δ–45.9 (q, second order spectrum with line spacings of 48 and 6 Hz and Pt satellites, J$_{Pt-P}$=2361 Hz). IR (thin film, cm$^{-1}$): 3410 (s), 2957 (w), 1694 (m), 1587 (m), 1464 (w), 1436 (m), 1101 (s), 1046 (m). High resolution mass spectrum (FAB) calc. m/z=791.10486 for C$_{34}$H$_{32}$ONP$_2$S$_2$$^{195}$Pt; found 791.10790. UV-vis (λ(nm), ε, CH$_2$Cl$_2$): 15, 351 (5500), 415 (520); 15H$^+$, 335 (4300), 450 (1900).

(dppp)Pt{S$_2$C$_2$(2-pyridyl)(CH$_2$CH$_2$OH)}, 16

Prepared and isolated as described for complex 15 using (200 mg, 0.232 mmol) of 14. Complex 16 was isolated in 92% yield (175 mg, 0.214 mmol). $^1$H NMR (CDCl$_3$): δ8.19 (m, 1H, C$_5$H$_4$N), 7.72 (m, 1H, C$_5$H$_4$N), 7.52–7.44 (m, 8H, PC$_6$H$_5$), 7.38–7.24 (m, 12H, PC$_6$H$_5$ and 1H, C$_5$H$_4$N), 6.85 (m, 1H, C$_5$H$_4$N), 3.72 (t, 2H, CH$_2$O, J$_{H-H}$=7 Hz), 2.76 (t, 2H, CH$_2$, J$_{H-H}$=7 Hz), 2.69 (m, 4H, PC$_3$H$_6$), 2.07 (m, 2H, PC$_3$H$_6$). $^{31}$P NMR (CDCl$_3$): δ–3.88 (br s, with Pt satellites, J$_{Pt-P}$=2646 Hz. There is no splitting of the center peak, but the upfield $^{195}$Pt satellite has splitting of 7 Hz). IR (thin film, cm$^{-1}$): 3418 (s), 2958 (w), 1694 (m), 1652 (m), 1588 (m), 1464 (w), 1436 (m), 1261 (m), 1101 (s). High-resolution mass spectrum (FAB) calc. m/z=819.13617 for $C_{36}H_{36}ONP_2S_2{}^{195}Pt$; found 819.13419. UV-vis ($\lambda$(nm), $\epsilon$, $CH_2Cl_2$): 16, 355 (5800), 405 (550); 16H$^+$, 340 (4000), 457 (1700).

[(dppm)Pt{$S_2C_2(CH_2CH_2$-N-2-pyridinium)}][BPh$_4$], 18

Complex 15 (150 mg, 0.189, mmol) was dissolved in dry pyridine (20 mL) and cooled to −10° C. To this solution was added p-toluenesulfonylchloride (72 mg, 0.378 mmol). The reaction mixture was allowed to warm to room temperature over 1 hour, and the reaction was quenched by the addition of 1 mL of water. The pyridine solution was subsequently removed in vacuo. The resulting solid was dissolved in 5 mL of MeOH, to which 1 mL of a NaBPh$_4$ saturated MeOH solution was added. Complex 18 was isolated in 60% yield (125 mg, 0.114 mmol) by filtration of the red solid, which was washed with 3×5 mL of MeOH. $^1$H NMR (CDCl$_3$): $\delta$8.41 (m, 1H, C$_5$H$_4$N), 7.64–7.57 (m, 8H, PC$_6$H$_5$, and 1H C$_5$H$_4$N), 7.41–7.27 (m, 12H, PC$_6$H$_5$ and 1H, C$_5$H$_4$N), 7.15–7.09 (m, 9H, B(C$_6$H$_5$)$_4$ and 1H, C$_5$H$_4$N), 6.88–6.65 (m, 9H, B(C$_6$H$_5$)$_4$), 6.46–6.40 (m, 2H, B(C$_6$H$_5$)$_{4l}$), 4.94 (t,2H, PCH$_2$, $J_{P-H}$=11 Hz), 3.34 (t, 2H, CH$_2$, $J_{H-H}$=7 Hz), 2.62 (t, 2H, CH$_2$, $J_{H-H}$=7 Hz). $^{31}$P NMR (DMSO): $\delta$47.3 (q, second order spectrum with major line spacings of 76 and 10 Hz and Pt satellites, $J_{Pt-P}$=2380 Hz). IR (thin film, cm$^{-1}$): 3054 (w), 2960 (w), 1621 (s), 1495 (s), 1436 (s), 1360 (w), 1263 (m), 1101 (m). High resolution mass spectrum (FAB) calc. m/z=773.09430 for $C_{34}H_{30}NP_2S_2{}^{195}Pt$; found 773.09658. UV-vis ($\lambda$(nm), $\epsilon$, $CH_2Cl_2$): 18, 350 (10700), 480 (3400).

[(dppp)Pt{$S_2C_2(CH_2CH_2$-N-2-pyridinium)}][BPh$_4$], 20

Prepared and isolated as described for complex 18, using (150 mg, 0.183 mmol) of 17 and p-toluenesulfonylchloride (69 mg, 0.366 mmol). Complex 20 was isolated in 73% yield (142 mg, 0.133 mmol). $^1$H NMR (CDCl$_3$): $\delta$8.42 (m, 1H, C$_5$H$_4$N), 7.66 (m, 1H, C$_5$H$_4$N), 7.41–7.37 (m, 8H, PC$_6$H$_5$), 7.31–7.23 (m, 12H, PC$_6$H$_5$ and 1H, C$_5$H$_4$N), 7.20–7.09 (m, 9H, B(C$_6$H$_5$)$_4$ and 1H, C$_5$H$_4$N), 6.86–6.79 (m, 9H, B(C$_6$H$_5$)$_4$), 6.68–6.61 (m, 2H, B(C$_6$H$_5$)$_4$), 3.18 (t, 2H, CH$_2$, $J_{H-H}$=7 Hz), 2.49 (m, 4H, PC$_3$H$_6$), 2.27 (t, 2H, CH$_2$, $J_{H-H}$=7 Hz), 1.94 (m, 2H, PC$_3$H$_6$). $^{31}$P NMR (CDCl$_3$): $\delta$−5.70 (br s, with Pt satellites, $J_{Pt-P}$=2674 Hz). IR (thin film, cm$^{-1}$): 3054 (w), 2998 (w), 1621 (s), 1494 (s), 1455 (m), 1436, (s), 1360 (w), 1280 (m), 1158 (m), 1101 (m), 911 (m), 731 (s), 704 (s). High resolution mass spectrum (FAB) calc. m/z=801.12561 for $C_{36}H_{34}NP_2S_2{}^{195}Pt$; found 801.12789. UV-vis ($\lambda$(nm), $\epsilon$, $CH_2Cl_2$): 20, 349 (12000), 499 (3300).

[(dppm)Pt{$C_2S_2$(N-methyl-2-pyridinium)(H)}][BPh$_4$], 21

Complex 5 (81 mg, 0.09 mmol) was dissolved in dry $CH_2Cl_2$, and methyl iodide (220 mg, 1.54 mmol) was added. The reaction mixture was stirred at 25° C. for 90 minutes, and the reaction was quenched by the addition of 1 mL of water. The $CH_2Cl_2$ solution was subsequently removed in vacuo. The resulting solid was dissolved in 5 mL of MeOH, to which 1 mL of a NaBPh$_4$ saturated MeOH solution was added. Complex 21 was isolated in 63% yield (66 mg, 0.060 mmol) by filtration of the red solid, which was washed with 3×5 mL of MeOH. $^1$H NMR (CDCl$_3$): $\delta$8.43 (m, 1H, C$_5$H$_4$N), 8.01 (d with $^{195}$Pt satellites, 1H, $J_{P-H}$, 7 Hz, $S_2C_2$H), $J_{PT-H}$=93 Hz), 7.57–7.51 (m, 8H, PC$_6$H$_5$ and 1H, C$_5$H$_4$N), 7.50–7.47 (m, 12H, PC$_6$H$_5$ and 1H, C$_5$H$_4$N), 7.43–7.37 (m, 9H, B(C$_6$H$_5$)$_4$), 7.11 (m, 1H, C$_5$H$_4$N), 6.95–6.84 (m, 9H, B(C$_6$H$_5$)$_4$), 6.76–6.73 (m, 2H, B(C$_6$H$_5$)$_4$), 2.48 (s, 3H, CH3), 1.93 (m, 2H, PC$_2$H$_4$). $^{31}$P NMR (CDCl$_3$): $\delta$47.1 (d with Pt satellites, $J_{P-P}$=10 Hz, $J_{Pt-P}$=3022 Hz), 45.8 (d with Pt satellites, $J_{P-P}$=10 Hz, $J_{Pt-P}$=2657 Hz). IR (thin film, cm$^{-1}$): 3055 (w), 2989 (w), 1581 (m), 1548 (m), 1461 (s), 1436 (s), 1262 (m), 1105 (s), 1031 (m). High-resolution mass spectrum (FAB) calc. m/z=775.10992 for $C_{34}H_{32}NP_2S_2{}^{195}Pt$; found 775.11088. UV-Vis ($\lambda$(nm), $\epsilon$, $CH_2Cl_2$): 21, 355 (9900), 417 (2900).

Immobilization of Complexes 1–4 in Cellulose Acetate

Cellulose acetate, triethylcitrate, and complexes 1–4 (0.1–0.5%) were dissolved in a minimum volume of acetone. The mixture was cast to yield a 0.5 mm film when the solvent was evaporated. The films were stored at 4° C. in the dark prior to use.

Immobilization of Complexes 1–4 in Cellulose Acetate-Butyrate

Cellulose acetate-butyrate, (CAB) tributylphosphate, and 1–4 (0.1–0.5%) were dissolved in a minimum volume of acetone. The mixture was cast to yield a 0.5 mm film when the solvent was evaporated. The films were stored at 4° C. in the dark prior to use.

Immobilization of Complexes 1–4 in GE RTV-118

GE RTV-118, a commercially available silicon elastomer from General Electric, was cast into a 0.5 mm-thick film by pressing the elastomer between two wax-coated LEXAN plates which are separated by a 0.5 mm thick anodized aluminum template. The elastomer was allowed to cure in place for four days. The film was then impregnated by immersing the cured film in a $CH_2Cl_2$ solution of complexes 1–4 for 30 minutes. The loading of the lumiphores was between 0.1–1%, based on the molar extinction coefficients of the metal complexes. An alternative method is to include complexes Ia–4 in silicone prior to polymerization at between 0.05 –5% loading, preferably 0.1–1% loading. This material can then be cast into a film by any standard method, as would be readily known to one skilled in the art.

This invention is not limited to these films; films such as polyvinylchloride, other silicones (GE RTF-108), acrylamide/methacrylamide, nylon-polyamide membranes, styrenes, cellulose nitrates, and polysulfones can also be used. The plasticizer is not limited to triethyl acetate, tributyl phosphate, or polysiloxanes—other plasticizers that are used with the polymer can readily be used in the present invention. Nor is the invention limited to the percentage ranges shown. In fact, varying the plasticizer and sensor loading can be used to vary sensitivity of the polymer-encapsulated sensor. These results demonstrate that a new method for detecting molecular oxygen has been developed using an immobilized emissive heterocyclic substituted platinum 1,2-enedithiolate.

Standardizing an Emitter

A polymer strip containing an immobilized lumiphore was attached to a quartz slide and placed in a fluorescence cuvette (2.8 mL) with a screw cap/septum lid. The slide was positioned at 45° to the front face of the square cuvette. The cuvette was next filled with deaerated water, or biological buffer, to a zero volume head space. The fluorescence spectrum FIG. 1 was recorded using a SLM-AB2 spectrofluorometer. Dioxygen was added to the cuvette via the introduction of aerated water or buffer (typically in 0.2 mL aliquots), while the zero volume head space was maintained and a fluorescence spectrum recorded. The dioxygen addition and fluorescence measurement steps were repeated until the dioxygen concentration was 2.5×10$^{-4}$ M.

Figure 2:
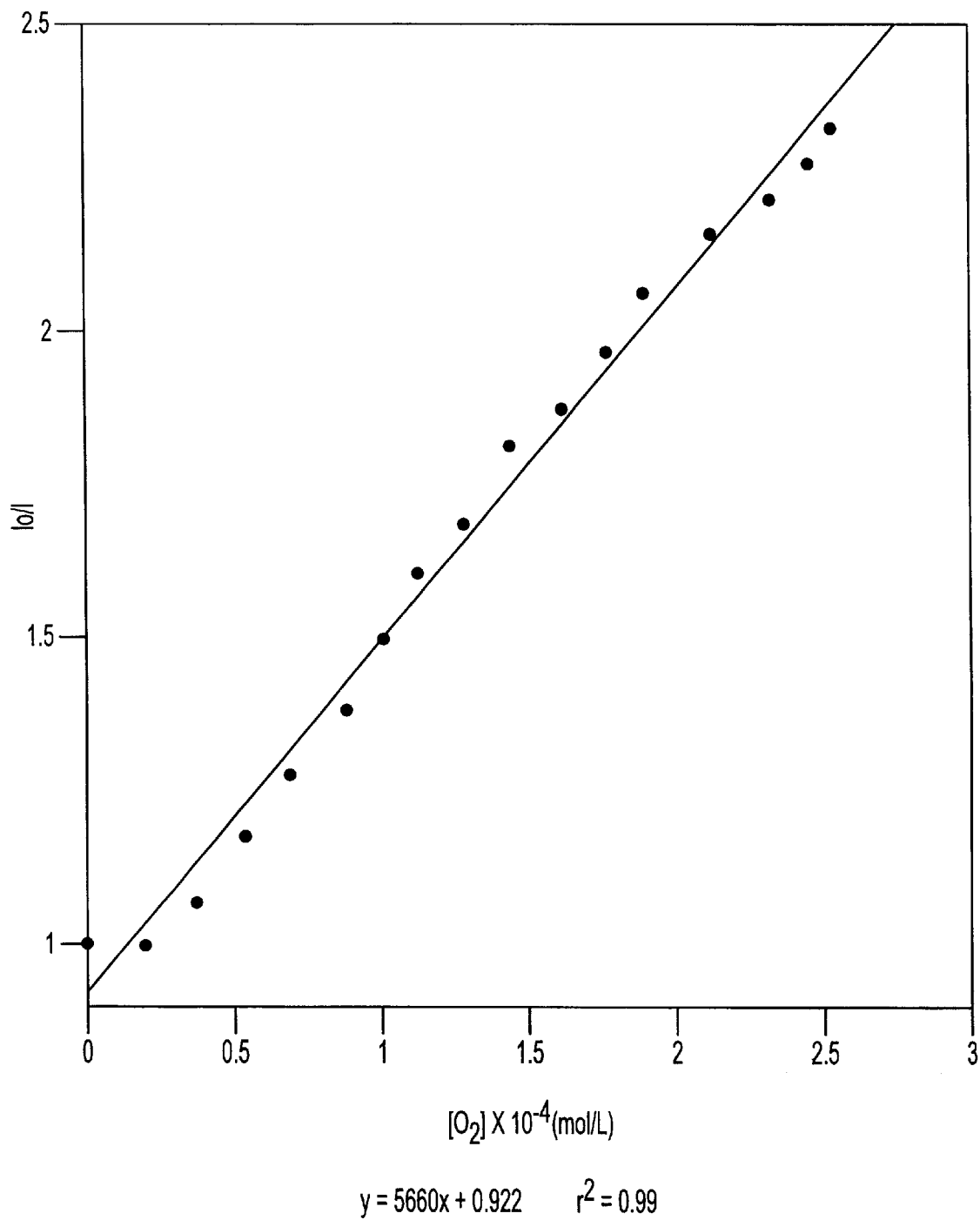
FIG. 2 is a plot of Io/I verses dioxygen concentration used to standardize the dioxygen-sensing GE RTV-118 film (0.5 mm thick) which contains Complex 1a at a 0.1% loading. The film is mounted on a quartz slide and placed in a deoxygenated 50 mM potassium phosphate buffer (pH 7) filled cuvette with a zero volume head space. The slide is held at approximately 45° to the source and detector of a SLM-AB2 spectrofluorometer. The dioxygen concentration is increased by adding aerated buffer to the cuvette while maintaining a zero volume head space. The intensities, Io and I, are based on the $^1$ILCT*/$^3$ILCT* emission ratio. The $^1$ILCT* and $^3$ILCT* emission intensities were obtained following deconvolution of the emission spectra after each dioxygen addition.
Figure 3:
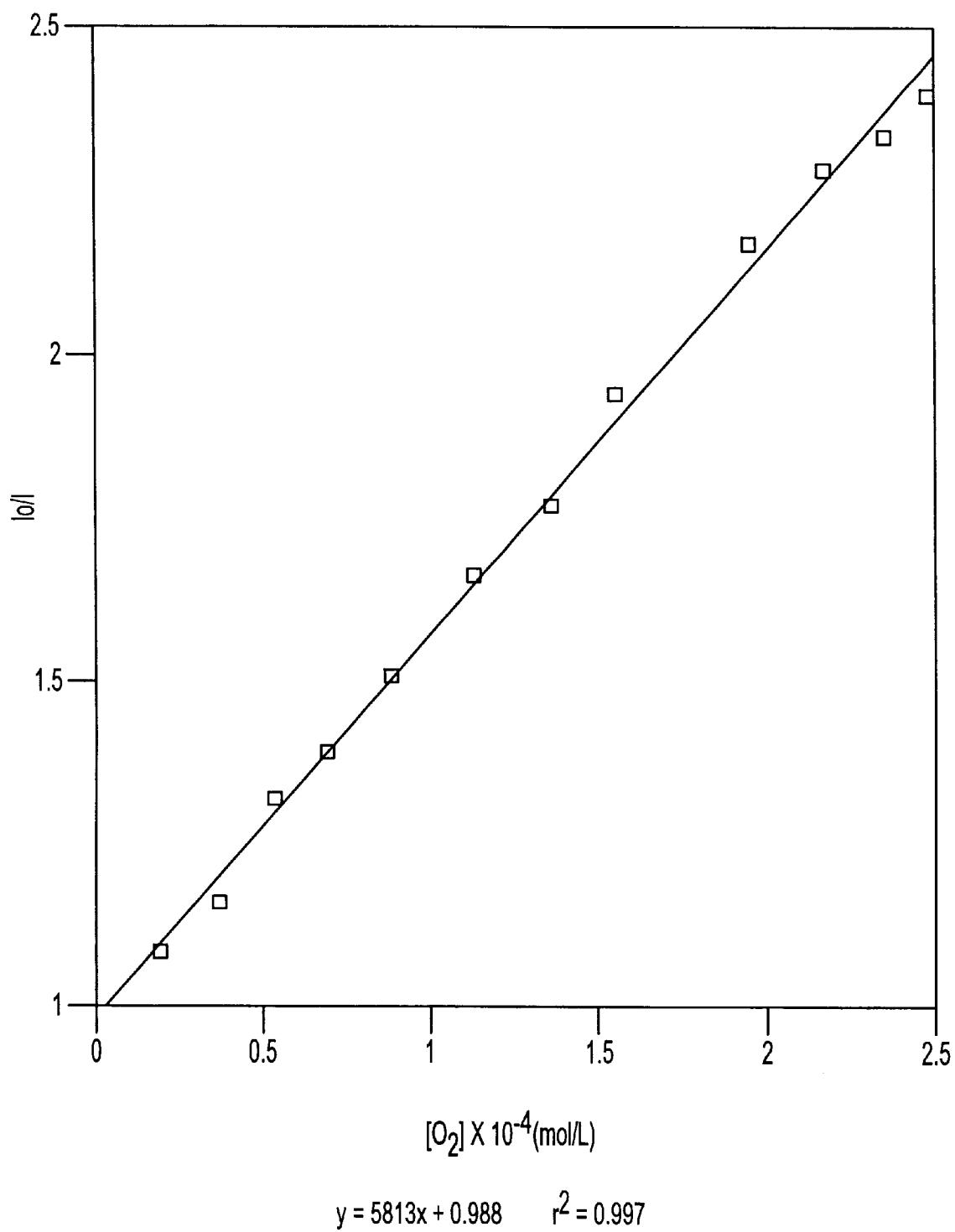
FIG. 3 is a plot of Io/I verses dioxygen concentration used to standardize the dioxygen-sensing CAB film (0.5 mm thick) which contains Complex 1 at a 0.5% by wt. The film is mounted on a quartz slide and placed in a deoxygenated water (pH 7) filled cuvette with a zero volume head space. The slide is held at approximately 45° to the source and detector of a SLM-AB2 spectrofluorometer. The dioxygen concentration is increased by adding aerated water to the cuvette while maintaining a zero volume head space. The intensities Io and I are based upon the relative $^1$ILCT*/$^3$ILCT* emission ratio. The $^1$ILCT*/$^3$ILCT* emission ratios were obtained following deconvolution of the emission spectra after each dioxygen addition.

The data from this standardization can be treated in one of two ways: 1) the intensity of the $^1$ILCT* and $^3$ILCT* emissions can be noted directly from the spectrum; or 2) the spectra can be deconvoluted using PeakFit (Jandel Scientific) and the intensity of the $^1$ILCT* and $^3$ILCT* emissions noted. In both cases, Io/I is plotted versus [O$_2$] where Io=$^3$ILCT* Intensity/$^1$ILCT* Intensity (initial) and I=$^3$ILCT* Intensity/$^1$ILCT* Intensity (at some [O$_2$]). The plots are fit to Io/I=m[O$_2$]+b where m=slope and b is the y intercept. This is a ratiometric adaptation of the Stern-Volmer plot. The intercept should be 1. Standardization curves are shown in FIGS. 2 and 3 for a RTV-118 film containing complex 1 and a CAB film containing complex 1, respectively. Once the values for m and b are obtained for a given film, the film can be used to determine the dioxygen concentration of an unknown solution. The Io/I value of the film placed in the unknown solution is recorded and by using [O$_2$]=(Io/I−b)/m the [O$_2$] can be determined.

While mounting and measurement procedures would be different if the emitters were used as a fiber optic tip or to encapsulate a diode, the data treatment for standardization would be similar to that described.

EXAMPLE 1

Figure 4:
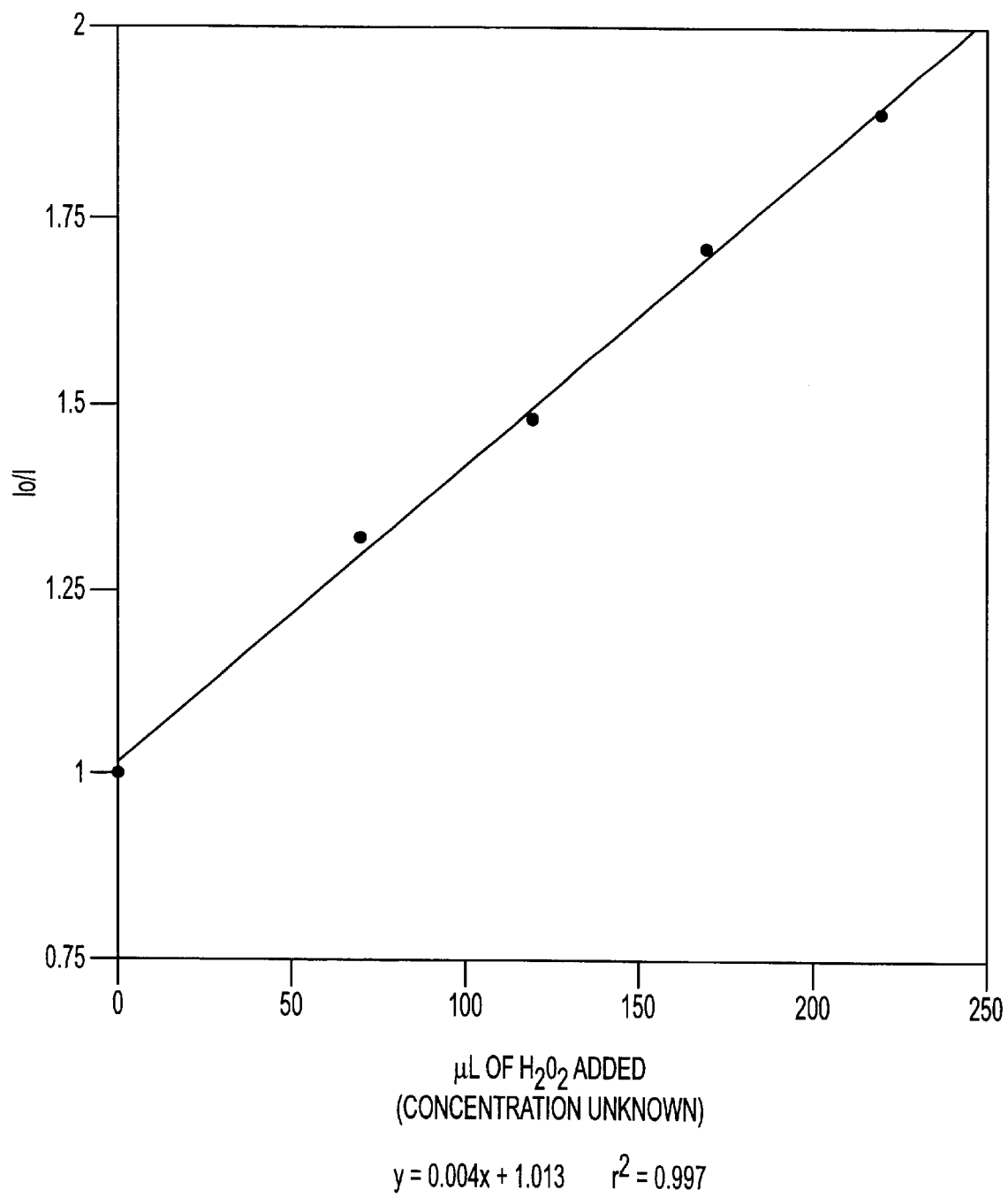
FIG. 4 is a plot of Io/I verses addition of an unknown $H_2O_2$ solution. The plot is used to standardize the $H_2O_2$ concentration. The GE RTV-118 Film (0.5 mm thick) contains Complex 1a at a 0.1% loading. The film is mounted on a quartz slide that is placed in a deoxygenated 50 mM potassium phosphate buffer (pH 7) containing 12 units of catalase (excess) filled cuvette with a zero volume head space. The slide is held at approximately 45° to the source and detector of a SLM-AB2 spectrofluorometer. $H_2O_2$ is added and converted to dioxygen (½ mole) and water (½ mole) by catalase. The $H_2O_2$ concentration of this unknown solution was determined to be 450 $\mu$M and was confirmed by a standard iodometric titration of the $H_2O_2$ solution.

Measuring Biological Dioxygen Production by Catalase and Determining [H$_2$O$_2$] of an Unknown Solution Unlike many other lumiphores, the emissions from complexes 1–4 are unaffected by mM H$_2$O$_2$. As such, these complexes can be used to monitor the production of O$_2$ from H$_2$O$_2$ by catalase. By using an immobilized lumiphore and the enzyme catalase, it is not only possible to evaluate the kinetics of dioxygen production by this enzyme, but also to standardize H$_2$O$_2$ solutions of unknown concentration. For this demonstration of the utility of these immobilized dioxygen sensing lumiphores, a GE RTV-118 film (0.5 mm thick) containing complex 1 at a 0.1 % loading (platinum loading 0.2 ppm) was mounted on a quartz slide and placed in a fluorescence cuvette (2.8 mL) with a screw cap/septum lid. The slide was positioned at 45° to the front face of the square cuvette. To the cuvette was added deoxygenated 50 mM potassium phosphate buffer (pH 7), and the film was standardized as described (see above Standardizing an Emitter) by the addition of aerated buffer to obtain the slope, m. The buffer was removed and replaced with deaerated 50 mM potassium phosphate buffer (pH 7) containing excess catalase (12 units). An unknown H$_2$O$_2$ solution was added and a zero volume head space maintained. The H$_2$O$_2$ was converted to dioxygen (½mole) and water (½mole) by catalase. The luminescence spectra was recorded and deconvoluted using PeakFit (Jandel Scientific) where the intensity of the $^1$ILCT* and $^3$ILCT* emissions recorded. The addition of H$_2$O$_2$ was repeated several times and the luminescence spectra recorded, see FIG. 4. The dioxygen produced was determined for each addition of H$_2$O$_2$ from Io/I measurements knowing m, and using [O$_2$]=(Io/I−b)/m for this film in this buffer. The [H$_2$O$_2$] concentration of the unknown solution was determined by averaging the values determined at each point. The [H$_2$O$_2$] determined using the catalase/dioxygen sensor was within experimental error of the value determined by an iodometric titration.

Figure 5A:
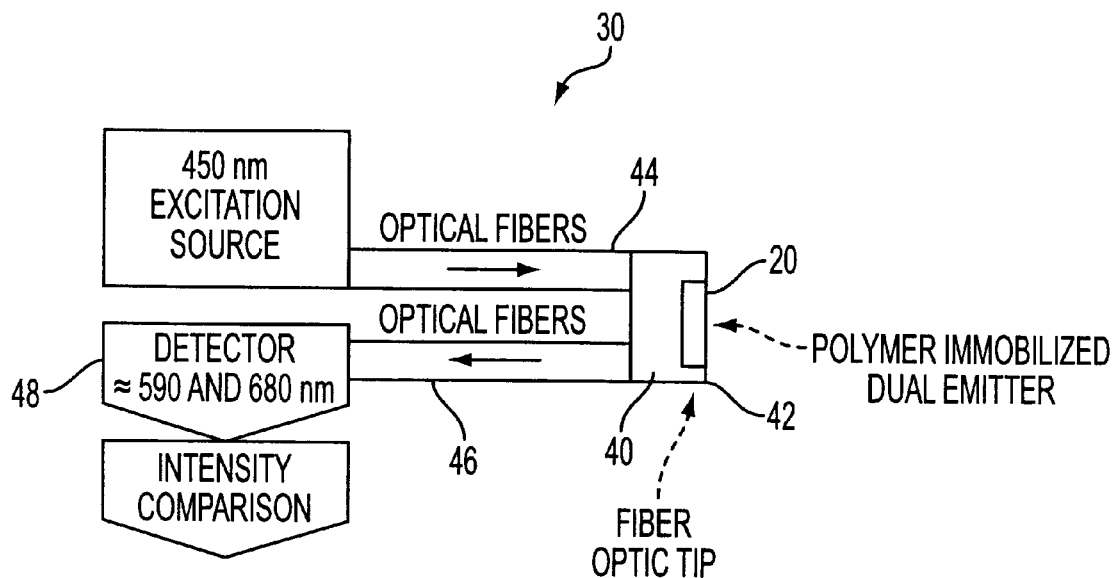
FIG. 5 is a schematic diagram of a detector system employing a sensor containing the novel luminophore of the invention.
Figure 5B:
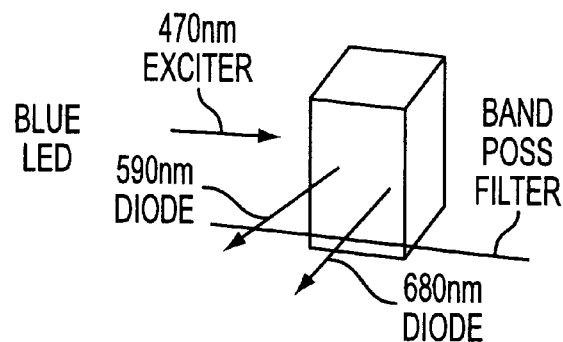

As shown in FIG. 5, the sensor 20 of the invention can be used in a detector system 30 for detecting emissions at 587 and 679 nm. Sensor 20 can be coated onto the distal end 42 of a fiber optic tip 40 wherein a first set of optical fibers 44 direct light energy to the sensor from a light source, such as an LED, and a second set of optical fibers 46 carry light energy from an excited source from the sensor to a detector 48. The changes in single-triplet luminescence ratio can be used to determine the analyte concentration. The present invention is distinguished from the prior use of intensity and lifetime/frequency modulation measurements with a single-emitting fluorescent or luminescent molecule.

As disclosed by Colvin et al. (*"A Novel Solid State Oxygen Sensor", John Hopkins APL Technical Digest*, Vol 17, No. 4 (1996)), a sensor encapsulated LED can be placed on an optical filter and photomultiplier. Excitation of the sensor by the LED allows analyte detection. The purpose of the optical filter is to absorb any scattered excitation light, while allowing the longer-wavelength fluorescent light to pass through to the photodiode detector. These molecules are suited for use with diode-based devices, for example when excited with blue LED, emission can be detected by separate photo-diodes.

All of the complexes, devices, and methods disclosed and claimed herein can be made without undue experimentation in light of the present disclosure. While the complexes, devices, and methods of this invention have been described in terms of preferred embodiments, it will be apparent to those skilled in the art that variations may be applied to the composition, methods, and in steps or the sequence of steps of the methods described without departing from the concept, spirit, and scope of the invention. More specifically, it will be apparent that certain complexes and devices, which are chemically related, may be substituted for the agents described here while the same or similar results will be achieved.

All such similar substitutions and modifications apparent to those of ordinary skill in the art are deemed to be within the spirit, scope, and concept of the invention as defined by the appended claims. All publications cited are hereby incorporated in their entirety by reference.

Definitions

1. Dioxygen

The elemental form of oxygen, the chemical entity O$_2$, molecular oxygen.

2. Analyte

Any chemical or biochemical entity for which a detection method has been or can be developed. Throughout the embodiment of this application, the principal analyte is dioxygen.

3. Emission

The release of a photon from an excited state which is not directly populated by photo-excitation. Emission is understood to include fluorescence [S1 to S0 (ground state)] and/or phosphorescence [T1 to S0].

4. Fluorescence

The release of a photon from an excited state which is not directly populated by photo-excitation . Fluorescence is understood to mean generally an emission from S1 to S0 (ground state). A photo-emissive process which does not involve a spin state change from the ground state. Generally an emission from a short-lived excited state (10 ns or less at room temperature). Within this embodiment the emission from the $^1$ILCT* excited state with cannot be dioxygen quenched (see item 8).

5. Phosphorescence

The release of a photon from an excited state which is not directly populated by photo-excitation . Generally an emission from T1 to S0 (ground state). A photo-emissive process which does involve a spin state change from the ground state. Generally an emission from a triplet excited state. An emission from a long-lived excited state (100 ns or more at room temperature). Within this embodiment the $^3$ILCT* excited state which is dioxygen quenched (see item 8).

6. Luminescence

Luminescence is a general term used to describe either fluorescence or phosphorescence. It is also used to describe an emission from a molecules where the spin-state of the emissive state is unclear. Within this embodiment the emission from either the excited states assigned to $^1$ILCT* or $^3$ILCT* excited state or both.

7. ILCT

The acronym for an "intra-ligand charge-transfer transition". This denotes the actual electron and charge motion which accompanies photo-excitation. The electronic transition which leads to emission from the $^1$ILCT* and $^3$ILCT* excited states.

8. Quenching

Any process that increases the non-radiative decay of an emissive excited. The loss of emission from a photo-excited molecule induced by a second molecule referred to as the quencher. The loss of emission is accompanied by a decrease in the excited state lifetime of the photo-excited molecule. Generally resulting from electron, hydrogen atom, proton, or energy transfers from/or to the quencher molecule. Commonly a diffusional process with rates which can be predicted by well established thermodynamic parameters. A reversible process that does not lead to a chemical transformation of either the photoexcited molecule or the quencher molecule. Within this embodiment the specific decease in both the emission from, and the lifetime of a long-lived oxygen-quenchable $^3$ILCT* state. The decrease in the light emitted from the $^3$ILCT* excited state upon exposure to molecular oxygen.

9. Emission Quenching

In the present invention, the term emission quenching means the specific decease in both the emission from, and the lifetime of a long-lived oxygen-quenchable $^3$ILCT* state (see item 3).

10. Luminescence Quenching

Within this embodiment the specific decease in both the emission from, and the lifetime of a long-lived oxygen-quenchable $^3$ILCT* state (see item 3).

11. Dual Emitting Complexes

A metal complex with room-temperature emissions arising from both a singlet and triplet photo-excited state. A room-temperature emitting metal complex with clearly definable fluorescence and phosphorescence. Within this embodiment, a metallo-1,2-enedithiolate with emissions from both the $^1$ILCT* and $^3$ILCT* excited states. A metallo-1,2-enedithiolate where the $^3$ILCT* excited state is analyte quenchable while the $^1$LCT* excited state serves as a reference for the quenching event.

What is claimed:

1. $L_2Pt\{S_2C_2(2\text{-pyridine})(H)\}$ and luminescent salts thereof, wherein L2 is either dppe or dppm and wherein dppe is 1,2-bis(diphenylphosphino) ethane and dppm is 1,2-bis(diphenylphosphino) methane.

2. $L_2Pt\{S_2C_2(4\text{-pyridine})(H)\}$ and luminescent salts thereof, wherein L2 is dppe, dppm or dppp and wherein dppe is 1,2-bis(diphenylphosphino) ethane, dppm is 1,2-bis(diphenylphosphino) methane and dppp is 1,2-bis(diphenylphosphino) propane.

3. The compound $[dppe\ Pt\{S_2C_2(CH_2CH_2\text{-N-2-pyridinium})\}]^+$ and luminous salts thereof, wherein dppe is 1,2-bis(diphenylphosphino) ethane.

4. The compound $[L_2Pt\{S_2C_2(Me\text{-N-4-pyridinium})(H)\}]^+$ and luminous salts thereof, wherein L2 is dppe, dppm or dppp and wherein dppe is 1,2-bis(diphenylphosphino) ethane, dppm is 1,2-bis(diphenylphosphino) methane and dppp is 1,2-bis(diphenylphosphino) propane.

5. The compound $L_2Pt\{S_2C_2(CH_2CH_2\text{-N-2-pyridinium})\}]^+$ and luminous salts thereof, wherein L2 is dppe, dppm or dppp and wherein dppe is 1,2-bis(diphenylphosphino) ethane, dppm is 1,2-bis(diphenylphosphino) methane and dppp is 1,2-bis(diphenylphosphino) propane.

* * * * *